United States Patent
Zhang et al.

(10) Patent No.: US 10,715,503 B2
(45) Date of Patent: Jul. 14, 2020

(54) METHOD AND APPARATUS FOR SECURING COMMUNICATIONS USING MULTIPLE ENCRYPTION KEYS

(71) Applicant: Alibaba Group Holding Limited, Grand Cayman (KY)

(72) Inventors: Jia Zhang, Hangzhou (CN); Kai Li, Hangzhou (CN)

(73) Assignee: ALIBABA GROUP HOLDING LIMITED, Grand Cayman (KY)

( * ) Notice: Subject to any disclaimer, the term of this patent is extended or adjusted under 35 U.S.C. 154(b) by 305 days.

(21) Appl. No.: 15/570,817

(22) PCT Filed: May 5, 2016

(86) PCT No.: PCT/CN2016/081068
§ 371 (c)(1),
(2) Date: Oct. 31, 2017

(87) PCT Pub. No.: WO2016/180264
PCT Pub. Date: Nov. 17, 2016

(65) Prior Publication Data
US 2018/0159833 A1    Jun. 7, 2018

(30) Foreign Application Priority Data
May 13, 2015   (CN) .......................... 2015 1 0243756

(51) Int. Cl.
*H04L 29/06* (2006.01)
*G06F 21/62* (2013.01)
(Continued)

(52) U.S. Cl.
CPC ...... *H04L 63/0442* (2013.01); *G06F 21/6218* (2013.01); *G06F 21/6245* (2013.01);
(Continued)

(58) Field of Classification Search
CPC ............. G06F 21/6245; G06F 21/6218; H04L 9/3247; H04L 9/0866; H04L 9/3226;
(Continued)

(56) References Cited

U.S. PATENT DOCUMENTS 5,636,280 A   6/1997   Kelly
6,044,154 A   3/2000   Kelly
(Continued)

FOREIGN PATENT DOCUMENTS

CN   102243736 A   11/2011
CN   103152182 A   6/2013
CN   104182619 A   12/2014

OTHER PUBLICATIONS

Samydurai A, Revathi K, Prema P, Arulmozhiarasi D S, Jency J and Hemapriya S, "Secured Health Care Information exchange on cloud using attribute based encryption," 2015 3rd International Conference on Signal Processing, Communication and Networking (ICSCN), Chennai, 2015, pp. 1-5. (Year: 2015).*
(Continued)

*Primary Examiner* — Kari L Schmidt
(74) *Attorney, Agent, or Firm* — James J. DeCarlo; Greenberg Traurig, LLP

(57) ABSTRACT

The disclosure provides a method and an apparatus for acquiring an electronic file. The method for acquiring an electronic file includes: generating a first encryption key according to login information of a user of a terminal device at the time of logging in to a platform server and a first identifier corresponding to an information providing server that provides the electronic file; sending a first request message for acquiring the electronic file to the platform server; receiving the electronic file encrypted using a second encryption key and returned by the platform server according to the login information and the first request message; and generating a first decryption key according to the first
(Continued)

encryption key, and decrypting, using the first decryption key, the electronic file encrypted using the second encryption key, so as to obtain the decrypted electronic file. By means of the disclosed embodiments, private information concerning a user in an electronic file is not leaked by a platform server. Since a terminal device can obtain a decryption key without the need to perform key exchange with an information providing server, use by the user of the terminal device is facilitated.

19 Claims, 25 Drawing Sheets

(51) Int. Cl.
  *H04L 9/08* (2006.01)
  *H04L 9/32* (2006.01)
  *G16H 10/60* (2018.01)
  *G06Q 30/06* (2012.01)

(52) U.S. Cl.
  CPC ........... *H04L 9/0866* (2013.01); *H04L 9/321* (2013.01); *H04L 9/3226* (2013.01); *H04L 9/3236* (2013.01); *H04L 9/3247* (2013.01); *H04L 9/3268* (2013.01); *H04L 9/3297* (2013.01); *H04L 29/06* (2013.01); *G06Q 30/0601* (2013.01); *G16H 10/60* (2018.01); *H04L 2209/56* (2013.01)

(58) Field of Classification Search
  CPC ..... H04L 9/321; H04L 9/3297; H04L 9/3268; H04L 9/3236; H04L 63/0442
  See application file for complete search history.

(56) References Cited

U.S. PATENT DOCUMENTS

| | | | |
|---|---|---|---|
| 6,263,435 B1 | 7/2001 | Dondeti et al. | |
| 6,734,886 B1* | 5/2004 | Hagan | G06F 21/6254 707/E17.109 |
| 6,874,085 B1* | 3/2005 | Koo | H04L 63/0428 713/165 |
| 6,947,556 B1 | 9/2005 | Matyas et al. | |
| 7,181,017 B1* | 2/2007 | Nagel | H04L 9/0825 380/282 |
| 7,587,366 B2* | 9/2009 | Grim, III | G06Q 20/40 705/44 |
| 7,661,146 B2 | 2/2010 | Karimzadeh et al. | |
| 7,908,487 B2 | 3/2011 | Williams et al. | |
| 8,042,193 B1* | 10/2011 | Piliouras | H04L 9/3236 713/169 |
| 8,212,677 B2 | 7/2012 | Ferguson | |
| 8,275,632 B2* | 9/2012 | Awaraji | G06F 19/328 705/2 |
| 8,275,850 B2* | 9/2012 | Kohan | G06F 21/6254 709/212 |
| 8,498,884 B2 | 7/2013 | Maitland et al. | |
| 8,549,007 B1* | 10/2013 | Wormley | G06F 16/13 707/741 |
| 8,552,868 B1 | 10/2013 | Ferguson | |
| 8,600,895 B2* | 12/2013 | Felsher | G06F 19/328 705/50 |
| 8,752,153 B2* | 6/2014 | Vysogorets | G06F 21/34 713/170 |
| 8,849,718 B2 | 9/2014 | Dala et al. | |
| 9,141,758 B2 | 9/2015 | Kress et al. | |
| 9,158,933 B2 | 10/2015 | Banks et al. | |
| 9,654,288 B1* | 5/2017 | Howell | H04L 9/0861 |
| 9,998,438 B2* | 6/2018 | Sinha | G06F 21/44 |
| 2003/0018495 A1 | 1/2003 | Sussman | |
| 2003/0223585 A1* | 12/2003 | Tardo | H04L 9/3226 380/277 |
| 2004/0172295 A1* | 9/2004 | Dahlin | G06F 19/3456 705/2 |
| 2006/0004588 A1* | 1/2006 | Ananda | G06Q 10/00 705/67 |
| 2006/0059346 A1* | 3/2006 | Sherman | H04L 63/0823 713/175 |
| 2006/0206932 A1* | 9/2006 | Chong | H04L 63/0807 726/10 |
| 2006/0259330 A1* | 11/2006 | Schranz | G06F 19/328 705/3 |
| 2007/0180259 A1 | 8/2007 | Bulot et al. | |
| 2008/0040602 A1* | 2/2008 | Williams | H04L 9/30 713/153 |
| 2008/0222042 A1 | 9/2008 | Moore et al. | |
| 2009/0103726 A1 | 4/2009 | Ahmed | |
| 2010/0030690 A1* | 2/2010 | Herlitz | G06F 21/6245 705/50 |
| 2010/0169218 A1 | 7/2010 | Wang et al. | |
| 2010/0262545 A1* | 10/2010 | Herlitz | G06Q 10/00 705/51 |
| 2011/0123027 A1* | 5/2011 | Gotthardt | G06F 21/606 380/270 |
| 2012/0036360 A1* | 2/2012 | Bassu | H04L 9/3228 713/168 |
| 2013/0110540 A1 | 5/2013 | Kimberling | |
| 2014/0156296 A1 | 6/2014 | Stenzler et al. | |
| 2014/0236635 A1 | 8/2014 | Liberty et al. | |
| 2014/0344943 A1* | 11/2014 | Todeschini | G06F 21/6209 726/26 |
| 2015/0026784 A1* | 1/2015 | Kurkure | H04L 63/083 726/7 |
| 2015/0172291 A1* | 6/2015 | Zhang | H04L 9/3226 726/7 |
| 2015/0213204 A1 | 7/2015 | Bose et al. | |
| 2015/0220746 A1* | 8/2015 | Li | G06Q 50/24 713/193 |
| 2015/0254463 A1* | 9/2015 | Ryhorchuk | G06F 21/602 713/156 |
| 2015/0324605 A1* | 11/2015 | Yoon | G06F 21/31 726/28 |
| 2016/0147944 A1* | 5/2016 | Douglass | G06F 21/31 705/51 |
| 2016/0147945 A1* | 5/2016 | MacCarthy | G06F 21/6254 705/51 |
| 2016/0275309 A1* | 9/2016 | Austin | H04L 63/06 |
| 2016/0378949 A1* | 12/2016 | Fu | H04L 63/10 705/2 |

OTHER PUBLICATIONS

Li, Zhuo-Rong, et al. "A secure electronic medical record sharing mechanism in the cloud computing platform." 2011 IEEE 15th international symposium on consumer electronics (ISCE). IEEE, 2011,pp. 98-103. (Year: 2011).*

Abbadi, Imad M., et al. "Trustworthy middleware services in the cloud." Proceedings of the third international workshop on Cloud data management. 2011, pp. 33-40. (Year: 2011).*

Avancha, Sasikanth, Amit Baxi, and David Kotz. "Privacy in mobile technology for personal healthcare." ACM Computing Surveys (CSUR) 45.1 (2012): 1-54. (Year: 2012).*

Extended European Search Report to corresponding EP Application No. 16792114.7 dated Oct. 30, 2018 (12 pages).

International Search Report to corresponding International Application No. PCT/CN2016/081068 dated Jul. 25, 2016 (2 pages).

* cited by examiner

METHOD AND APPARATUS FOR SECURING COMMUNICATIONS USING MULTIPLE ENCRYPTION KEYS

The application claims priority to Chinese Patent Application No. 201510243756.3, filed on May 13, 2015, and entitled "METHOD AND APPARATUS FOR ACQUIRING ELECTRONIC FILE" and PCT Application No. PCT/CN2016/081068 filed May 5, 2016, and entitled "METHOD AND APPARATUS FOR ACQUIRING ELECTRONIC FILE," both of which are incorporated herein by reference in their entirety.

BACKGROUND

Technical Field

The disclosure relates to the field of cryptography, and in particular, to a method and apparatus for securing communications between multiple parties using multiple encryption keys.

Description of the Related Art

To ensure the safety and effectiveness of drug usage, when selling prescription drugs, pharmacies require patients to provide paper prescriptions issued by doctors as purchasing vouchers. With the popularization of the Internet in all industries, Internet-based electronic prescriptions have also been vigorously promoted by e-commerce platforms. Electronic prescriptions have the advantages of standard formats, complete and clear contents, and the convenience of querying for historical records by doctors and patients over paper prescriptions, and are the basis for promoting selling prescription drugs online at a large scale. To enable users and pharmacies to use electronic prescriptions conveniently, an electronic prescription platform ("EPP") needs to be established on the Internet, to facilitate view and use of prescriptions by all parties. Since an electronic prescription contains a patient's private information (e.g., the patient's name, ID number, mobile phone number, birth date, social security number, illness, and drugs prescribed by the doctor), which can be accessed through the Internet anywhere and anytime, the private information of the patient is susceptible to malicious attacks and theft. Thus, private information concerning the patient in the electronic prescription needs a more secure means of protection.

BRIEF SUMMARY

Accordingly, the present disclosure provides a novel technical solution which can solve the technical problems in current systems of incomplete protection on private information concerning a user in an electronic file.

To achieve the objective above, the present disclosure provides the following technical solutions.

According to a first aspect of the disclosure, a method for acquiring an electronic file is provided, which is executed by a terminal device and comprises: generating a first encryption key according to login information of a user of the terminal device at the time of logging in to a platform server and a first identifier corresponding to an information providing server that provides an electronic file, wherein the information providing server is used for providing the electronic file to the terminal device; sending a first request message for acquiring the electronic file to the platform server, wherein the first request message includes the first identifier and a second identifier of the electronic file; receiving the electronic file encrypted using a second encryption key and returned by the platform server according to the login information and the first request message, wherein the second encryption key is generated from the first encryption key, the first identifier, and the second identifier; and generating a first decryption key according to the first encryption key, and decrypting, using the first decryption key, the electronic file encrypted using the second encryption key, so as to obtain the decrypted electronic file.

According to a second aspect of the disclosure, a method for acquiring an electronic file is provided, which is executed by a terminal device and comprises: sending a second request message for acquiring an electronic file to a platform server, wherein the second request message includes a first identifier corresponding to an information providing server that provides the electronic file, a second identifier of the electronic file, and a third identifier of a third-party user; after the platform server confirms that the third identifier has the right to view the electronic file and that the first identifier has a binding relationship with a user login name included in the login information, receiving a digital certificate of the third-party user that is returned by the platform server; acquiring a public key of the third-party user from the digital certificate; generating the second encryption key through a hash operation according to the first encryption key, the first identifier, and the second identifier; and encrypting the second encryption key using the public key of the third-party user, and sending the first identifier, the second identifier, and the encrypted second encryption key to the platform server.

According to a third aspect of the disclosure, a method for acquiring an electronic file is provided, which is executed by a platform server and comprises: receiving a first request message from a terminal device for acquiring an electronic file, wherein the first request message includes a first identifier corresponding to an information providing server that provides the electronic file and a second identifier corresponding to the electronic file; determining a user registration name of a user of the terminal device on the information providing server through login information of the user on the platform server and the first identifier; sending the first identifier, the second identifier, and the user registration name to the information providing server after digitally signing them; receiving the electronic file encrypted by the information providing server using a second encryption key, wherein the second encryption key is generated from a first encryption key and the first identifier, and the first encryption key is generated according to the login information of the user of the terminal device logging in to the platform server and the first identifier; and sending the electronic file encrypted using the second encryption key to the terminal device.

According to a fourth aspect of the disclosure, a method for acquiring an electronic file is provided, which is executed by an information providing server and comprises: receiving a third request message from a platform server for acquiring an electronic file, wherein the third request message includes a first identifier corresponding to the information providing server and a second identifier of the electronic file; searching for the electronic file according to the second identifier; generating a second encryption key for encrypting the electronic file according to the first identifier, the second identifier, and a first encryption key, wherein the first encryption key is generated from login information of the terminal device on the platform server and the first identifier;

and sending the first identifier, the second identifier, and the electronic file that is encrypted using the second encryption key to the platform server.

According to a fifth aspect of the disclosure, an apparatus for acquiring an electronic file is provided, which is executed by a terminal device and comprises: a first generation module, configured to generate a first encryption key according to login information of a user of the terminal device at the time of logging in to a platform server and a first identifier corresponding to an information providing server that provides the electronic file, wherein the information providing server is used for providing the electronic file to the terminal device; a first sending module, configured to send a first request message for acquiring the electronic file to the platform server, wherein the first request message includes the first identifier and a second identifier of the electronic file; a first receiving module, configured to receive the electronic file encrypted using a second encryption key and returned by the platform server according to the login information and the first request message that is sent by the first sending module, wherein the second encryption key is generated from the first encryption key, the first identifier, and the second identifier; and a first decryption module, configured to generate a first decryption key according to the first encryption key generated by the first generation module, and decrypt, using the first decryption key, the electronic file encrypted using the second encryption key and received by the first receiving module, so as to obtain the decrypted electronic file.

According to a sixth aspect of the disclosure, an apparatus for acquiring an electronic file is provided, which is executed by a platform server and comprises: a seventh receiving module, configured to receive a first request message from a terminal device for acquiring an electronic file, wherein the first request message includes a first identifier corresponding to an information providing server that provides the electronic file and a second identifier corresponding to the electronic file; a third determining module, configured to determine a user registration name of a user of the terminal device on the information providing server through login information of the user on the platform server and the first identifier that is carried in the first request message received by the seventh receiving module; a seventh sending module, configured to send the first identifier, the second identifier, and the user registration name to the information providing server after digitally signing them; an eighth receiving module, configured to receive the electronic file encrypted by the information providing server using a second encryption key, wherein the second encryption key is generated from a first encryption key and the first identifier that is carried in the first request message received by the seventh receiving module, and the first encryption key is generated according to the login information of the user of the terminal device logging in to the platform server and the first identifier; and an eighth sending module, configured to send the electronic file encrypted using the second encryption key and received by the eighth receiving module to the terminal device.

According to a seventh aspect of the disclosure, an apparatus for acquiring an electronic file is provided, which is executed by an information providing server and comprises: a sixteenth receiving module, configured to receive a third request message from a platform server for acquiring an electronic file, wherein the third request message includes a first identifier corresponding to the information providing server and a second identifier of the electronic file; a search module, configured to search for the electronic file according to the second identifier received by the sixteenth receiving module; a second generation module, configured to generate a second encryption key for encrypting the electronic file according to the first identifier and the second identifier that are received by the sixteenth receiving module and a first encryption key, wherein the first encryption key is generated from login information of the terminal device on the platform server and the first identifier; and a seventeenth sending module, configured to send the first identifier, the second identifier, and the electronic file that is encrypted using the second encryption key generated by the second generation module to the platform server.

It can be seen from the aforementioned technical solutions that in embodiments of the disclosure, an electronic file requested by a terminal device is encrypted using a second encryption key. Since the second encryption key is generated from a first encryption key, a first identifier, and a second identifier, the terminal device can generate a first decryption key corresponding to the second encryption key according to the first encryption key, and decrypt, using the first decryption key, the electronic file encrypted using the second encryption key, so as to obtain the decrypted electronic file. In this way, private information concerning a user in an electronic file that is acquired from an information providing server is not leaked by a platform server. Since the second encryption key used for encrypting the electronic filed by the information providing server is generated from the first encryption key, the first identifier, and the second identifier, the terminal device can obtain a decryption key without the need to perform key exchange with the information providing server, thereby facilitating use by the user of the terminal device.

DETAILED DESCRIPTION OF THE EMBODIMENTS

Figure 1:
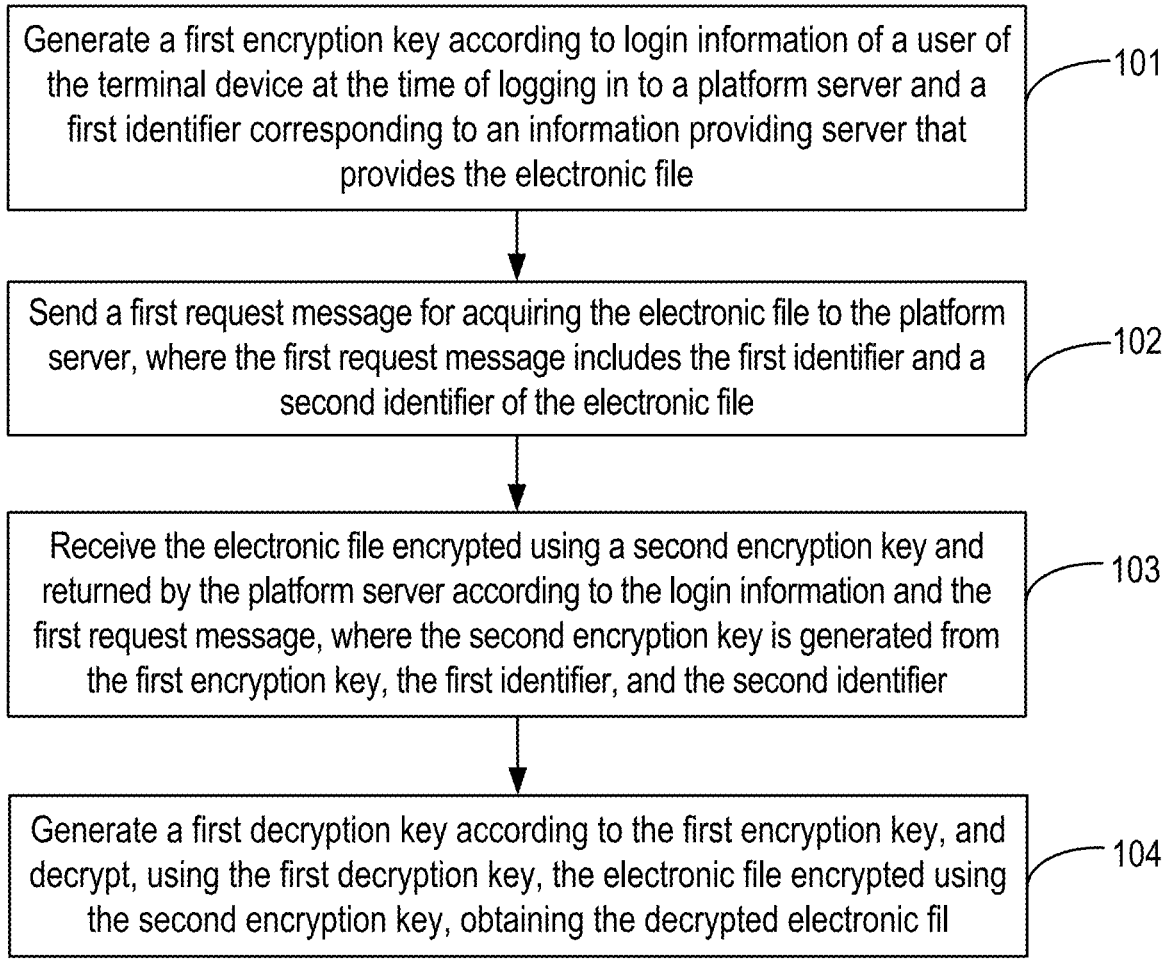
FIG. 1 is a flow diagram illustrating a method for acquiring an electronic file according to some embodiments of the disclosure.

Exemplary embodiments will be described in detail here, and examples thereof are shown in the drawings. The following description refers to the drawings in which the same numbers in different drawings represent the same or similar elements unless otherwise indicated. Implementations described in the following embodiments are not representative of all implementations consistent with the disclosure. Instead, they are merely examples of apparatuses and methods consistent with some aspects of the disclosure as recited in the appended claims.

The terms used in the disclosure are for the purpose of describing the embodiments only and are not intended to limit the disclosed embodiments. The singular forms "a", "an" and "the" used in the disclosure and the appended claims are also intended to include plural forms, unless the context clearly indicates otherwise. It should also be understood that the term "and/or" as used herein refers to and encompasses any or all possible combinations of one or more of the associated listed items.

It should be understood that although various types of information may be described using terms such as first, second, and third in the disclosure, such information should not be limited by these terms. These terms are only used to distinguish one type of information from another type of information. For example, first information may also be referred to as second information. Similarly, second information may also be referred to as first information without departing from the scope of the disclosure. Depending on the context, the word "if" as used herein may be construed to mean "when . . . " or "upon . . . " or "in response to determining".

In embodiments of the disclosure, an electronic file requested by a terminal device is encrypted using a second encryption key. Since the second encryption key is generated from a first encryption key, a first identifier, and a second identifier, the terminal device can generate a first decryption key corresponding to the second encryption key according to the first encryption key, and decrypt, using the first decryption key, the electronic file encrypted using the second encryption key, so as to obtain the decrypted electronic file. In this way, private information concerning a user in an electronic file that is acquired from an information providing server is not leaked by a platform server. Since the second encryption key used for encrypting the electronic filed by the information providing server is generated from the first encryption key, the first identifier, and the second identifier, the terminal device can obtain a decryption key without the need to perform key exchange with the information providing server, thereby facilitating use by the user of the terminal device.

Various embodiments are described in more detail below.

FIG. 1 is a flow diagram illustrating a method for acquiring an electronic file shown according to some embodiments of the disclosure. This embodiment may be implemented by a terminal device and includes the following steps.

Step 101: Generate a first encryption key according to login information of a user of the terminal device at the time of logging in to a platform server and a first identifier corresponding to an information providing server that provides the electronic file, where the information providing server is used for providing the electronic file to the terminal device.

Step 102: Send a first request message for acquiring the electronic file to the platform server, where the first request message includes the first identifier and a second identifier of the electronic file.

Step 103: Receive the electronic file encrypted using a second encryption key and returned by the platform server according to the login information and the first request message, where the second encryption key is generated from the first encryption key, the first identifier, and the second identifier.

Step 104: Generate a first decryption key according to the first encryption key, and decrypt, using the first decryption key, the electronic file encrypted using the second encryption key, obtaining the decrypted electronic file.

In step 101, the terminal device may generate a first encryption key according to login information of a user logging in to a platform server and a first identifier corresponding to an information providing server that provides the electronic file, the first encryption key may be regarded as a seed key (Seed) that is shared with the information providing server. Since the first encryption key may be generated from the login information and the first identifier, the terminal device does not need to save the seed key, so that the security of the electronic file encrypted using the seed key and user experience can be improved. In one embodiment, the seed key may be obtained through a hash operation, that is, Seed=Hash (HIS_ID, Username, Password), where HIS_ID is the first identifier, Username is a user login name in the login information, and Password is a login password in the login information. In one embodiment, the platform server may serve as a network platform connecting the terminal device and the information providing server and may be provided by an e-commerce platform, and different terminal devices and different information providing servers may transmit electronic files through the platform server. In one embodiment, the electronic file may be an electronic prescription, the information providing server may be a hospital information system ("HIS") on the hospital side, and the platform server may be an electronic prescription platform ("EPP") on the network side. In another embodiment, the electronic file may also be a social security file of the user on the terminal device side, the information providing server may be a social security service system on the social security center side, and the platform server may be a social security information platform on the network side. In yet another embodiment, the electronic file may also be a housing provident fund bill of the user on the terminal device side, the information providing server may be a provident fund service system on the housing provident fund management center side, and the platform server may be a provident fund information platform on the network side. It can be seen that the specific content of the electronic file is not limited in the disclosed embodiments, and any electronic file requiring encryption protection performed through the disclosed embodiments is the electronic file.

In step 102, the illustrated embodiment is described using an electronic prescription as an example of an electronic file. In this embodiment, the first request message may carry the first identifier. In this example, the first identifier is a hospital code (HIS_ID) corresponding to the user of the terminal device on an HIS, and the second identifier is a prescription number (P_ID) of the electronic prescription.

In step 103, after the EPP receives the first request message, the EPP verifies whether a user login name in the login information has a relationship with the first identifier (e.g., the hospital code), and if it is determined that the first identifier has a relationship with the user login name, the EPP acquires the electronic prescription corresponding to the second identifier from the HIS.

In step 104, the terminal device may generate a corresponding decryption key according to the first encryption key, and decrypt, using the decryption key, private information of the electronic prescription encrypted using the second encryption key. Also, the validity of the electronic prescription may also be verified through the decrypted private information.

In the illustrated embodiment, an electronic file requested by a terminal device is encrypted using a second encryption key. Since the second encryption key is generated from a first encryption key, a first identifier, and a second identifier, the terminal device can generate a first decryption key corresponding to the second encryption key according to the first encryption key. The terminal can also decrypt, using the first decryption key, the electronic file encrypted using the second encryption key, to obtain the decrypted electronic file. In this manner, private information concerning a user in an electronic file that is acquired from an information providing server is not leaked by a platform server. Since the second encryption key used for encrypting the electronic filed by the information providing server is generated from the first encryption key, the first identifier, and the second identifier, the terminal device can obtain a decryption key without the need to perform key exchange with the information providing server, thereby facilitating use by the user of the terminal device.

Figure 2:
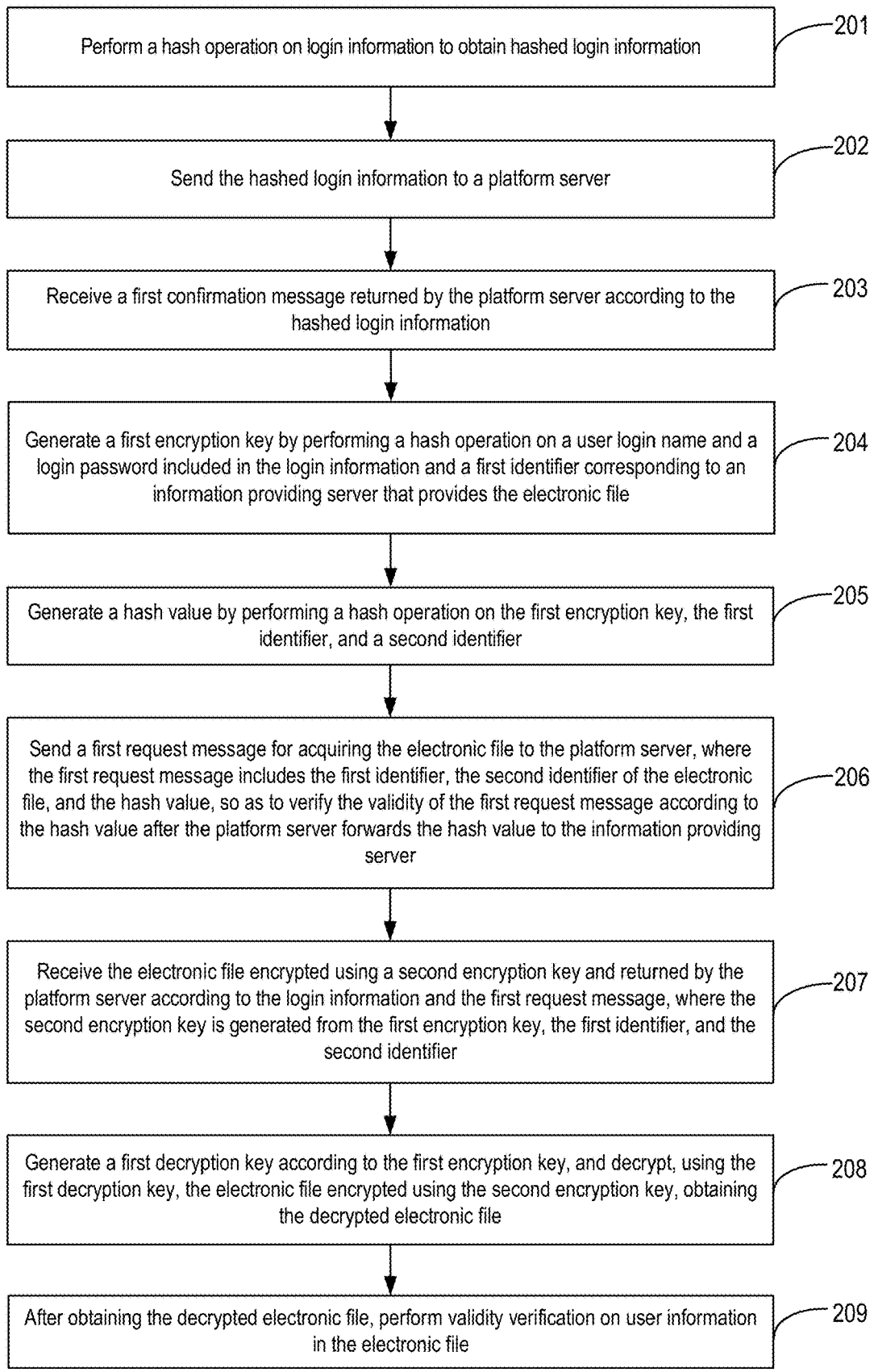
FIG. 2 is a flow diagram illustrating a method for acquiring an electronic file according to some embodiments of the disclosure.

FIG. 2 is a flow diagram illustrating a method for acquiring an electronic file according to some embodiments of the disclosure. The method includes the following steps.

Step 201: Perform a hash operation on login information to obtain hashed login information.

Step 202: Send the hashed login information to a platform server.

Step 203: Receive a first confirmation message returned by the platform server according to the hashed login information.

Step 204: Generate a first encryption key by performing a hash operation on a user login name and a login password included in the login information and a first identifier corresponding to an information providing server that provides the electronic file.

Step 205: Generate a hash value by performing a hash operation on the first encryption key, the first identifier, and a second identifier.

Step 206: Send a first request message for acquiring the electronic file to the platform server, where the first request message includes the first identifier, the second identifier of the electronic file, and the hash value, so as to verify the validity of the first request message according to the hash value after the platform server forwards the hash value to the information providing server.

Step 207: Receive the electronic file encrypted using a second encryption key and returned by the platform server according to the login information and the first request message, where the second encryption key is generated from the first encryption key, the first identifier, and the second identifier.

Step 208: Generate a first decryption key according to the first encryption key, and decrypt, using the first decryption key, the electronic file encrypted using the second encryption key, obtaining the decrypted electronic file.

Step 209: After obtaining the decrypted electronic file, perform validity verification on user information in the electronic file.

In step 201 to step 203, in one embodiment, the user login name (which may also be referred to as a user identifier) included in the login information may be a mobile phone number of the user. The terminal device may perform a hash operation on the mobile phone number, so the platform server cannot acquire real login information of the user of the terminal device when the platform server is logged in to using the user login name after the hash operation. Thereby, the method prevents an eavesdropper from stealing the login information of the user of the terminal device and the platform server from leaking the login information of the user of the terminal device.

Step 204 may be described with reference to the description of step 101 (described previously), the disclosure of which is not repeated herein but is incorporated by reference in its entirety.

In step 205, a hash operation of a hash-based message authentication code ("HMAC") is performed on the first identifier HIS_ID, the second identifier P_ID, and the first encryption key to obtain a hash value HMAC, so that the HIS can verify the validity of a first request message.

Step 206 to step 208 may be described with reference to the description of the steps 102 to step 104 (described previously), the disclosure of which is not repeated herein but is incorporated by reference in its entirety.

In step 209, after the decrypted electronic file is obtained, validity verification is performed on user information in the electronic file, to prevent the terminal device from obtaining an electronic file irrelevant to the user of the terminal device.

In this embodiment, on the basis of the beneficial technical effects of the aforementioned embodiment, a platform server is logged in to after a hash operation is performed on login information, so that the platform server cannot acquire real login information of a real user of a terminal device, thereby preventing an eavesdropper from stealing the login information of the user of the terminal device and the platform server from leaking the login information of the user of the terminal device. A hash operation is performed on a first identifier, a second identifier, and a first encryption key to obtain a hash value, so that an information providing server can verify the validity of a first request message that is received this time.

Figure 3:
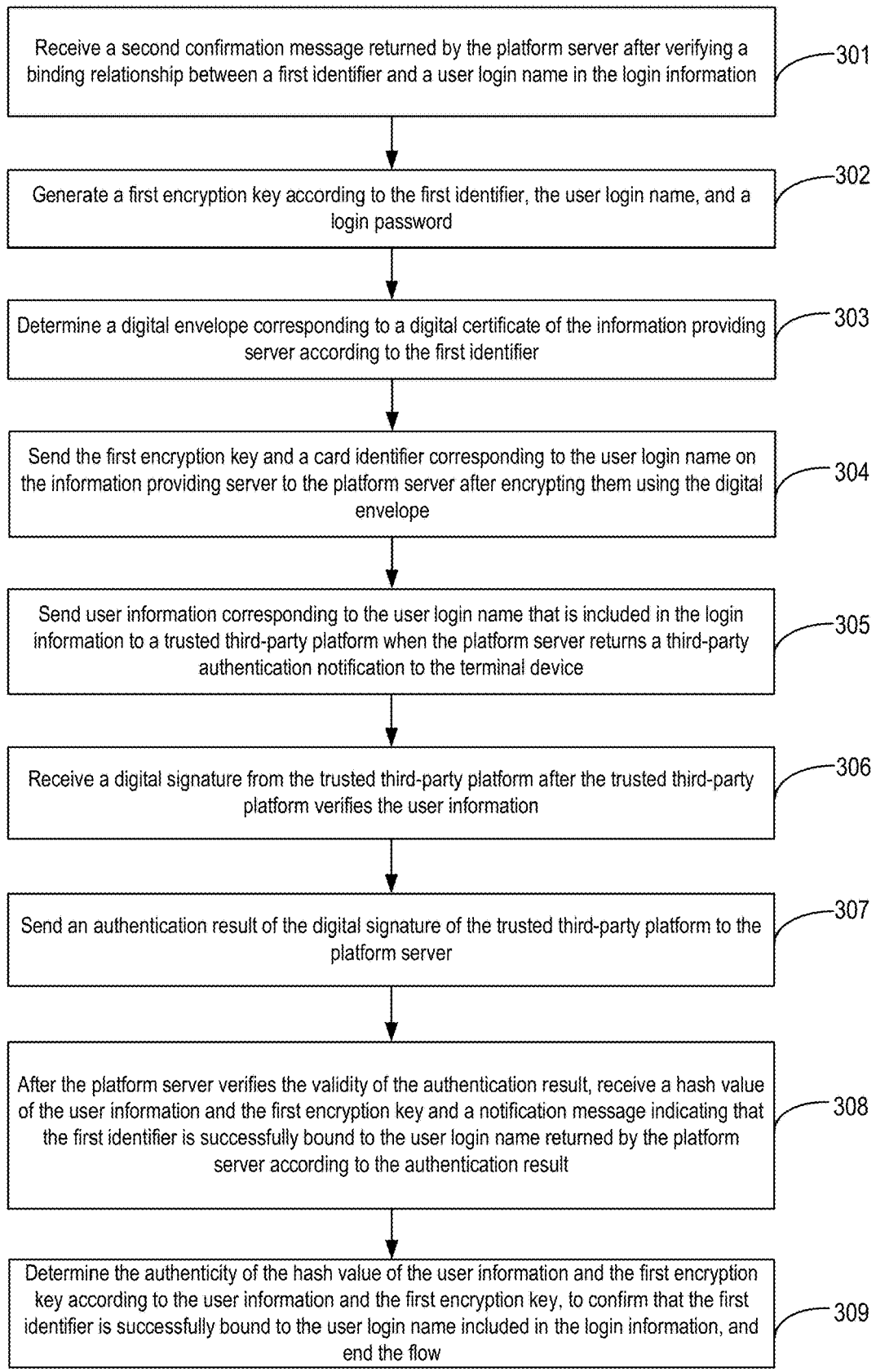
FIG. 3 is a flow diagram illustrating a method for acquiring an electronic file according to some embodiments of the disclosure.

FIG. 3 is a flow diagram illustrating a method for acquiring an electronic file according to some embodiments of the disclosure.

On the basis of the aforementioned embodiments discussed in connection with FIG. 1 or FIG. 2, the embodiment illustrated in FIG. 3 is described using a user login name needing to be bound to an information providing server and authorization and authentication in the process of acquiring an electronic prescription as an example. A user of a terminal device already registers with a platform server and has his corresponding user login name, and the user of the terminal device also registers with a trusted third-party ("TTP") platform, and the user of the terminal device already logs in to the platform server. As shown in FIG. 3, the method includes the following steps.

Step 301: Receive a second confirmation message returned by the platform server after verifying a binding relationship between a first identifier and a user login name in the login information. If the second confirmation message indicates that the first identifier does not have the binding relationship with the user login name, perform step 302. If the second confirmation message indicates that the first identifier has the binding relationship with the user login name, receive an electronic file encrypted using a second encryption key and returned by the platform server according to a first request message. Reference may be made to the aforementioned embodiment for the processing flow, which will not be described in detail in this embodiment.

Step 302: Generate a first encryption key according to the first identifier, the user login name, and a login password.

Step 303: Determine a digital envelope corresponding to a digital certificate of the information providing server according to the first identifier.

Step 304: Send the first encryption key and a card identifier corresponding to the user login name on the information providing server to the platform server after encrypting them using the digital envelope.

Step 305: Send user information corresponding to the user login name that is included in the login information to a trusted third-party platform when the platform server returns a third-party authentication notification to the terminal device.

Step 306: Receive a digital signature from the trusted third-party platform after the trusted third-party platform verifies the user information, where the digital signature is obtained by the trusted third-party platform signing a timestamp and a hash value of the user information using a private key of the trusted third-party platform.

Step 307: Send an authentication result of the digital signature of the trusted third-party platform to the platform server.

Step 308: After the platform server verifies the validity of the authentication result, receive a hash value of the user information and the first encryption key and a notification message indicating that the first identifier is successfully bound to the user login name returned by the platform server according to the authentication result.

Step 309: Determine the authenticity of the hash value of the user information and the first encryption key according to the user information and the first encryption key, to confirm that the first identifier is successfully bound to the user login name included in the login information, and end the flow.

In step 301 to step 303, a second confirmation message returned by the platform server after verifying a binding relationship between a first identifier and a user login name in login information is received. If the second confirmation message indicates that the first identifier does not have the binding relationship with the user login name, a user of the terminal device may generate a first encryption key based on a first identifier corresponding to the information providing server, and the user login name and a login password in the login information. The terminal device may request, based on the first identifier, the platform server for binding to the first identifier of the corresponding information providing server. The terminal device may send information required by the information providing server such as the generated first encryption key and a card identifier (Card_ID) corresponding to the user on the information providing server to the information providing server after encrypting the information using a digital envelope generated through a digital certificate that is provided by the information providing server.

In step 304, in one embodiment, if the information providing server is a hospital information server, the card identifier may be an identity of a medical card (for example, a card number of the medical card) of the user on the hospital information server. If the information providing server is a social security information server, the card identifier may be an identity of a social security card (for example, a card number of the social security card) of the user on a social security information server. If the information providing server is a provident fund information server, the card identifier may be an identity of a bank card (for example, a bank card number of provident funds) of the user on the provident fund information server.

In step 305, the terminal device may provide the user login name, the login password, and personal information of the user to be verified to a TTP platform based on a trusted third-party HyperText Transfer Protocol Secure (HTTPS) connection. In one embodiment, when the electronic file is an electronic prescription, file information may be identity information of a patient (Patient_Info).

In step 306 and step 307, after the TTP platform verifies the user information, the terminal device receives a timestamp of the TTP platform, a hash value of user real-name information, and a digital signature of the user information and the terminal device sends a verification result of the TTP to the platform server.

In step 308, in one embodiment, the platform server may establish a binding relationship between the user login name and the first identifier and save the binding relationship. In addition, the platform server may further establish a binding relationship between the user login name and a user registration name of the user corresponding to the user login name on the information providing server, and after the user logs in to the platform server using the user login name, the user registration name corresponding to the user login name on the information providing server of the first identifier can be determined. In one embodiment, through a hash value of the file information of the electronic file (in the situation that the electronic file is an electronic prescription, the file information is case information) and the first encryption key that is returned by the platform server to the terminal device, a second identifier of the electronic file and information indicating successful binding are forwarded to the terminal device, and the terminal device calculates the authenticity of the hash value through the first encryption key and the file information, so as to confirm successful binding.

In this embodiment, an identity of a user of a terminal device is authenticated based on a TTP platform that saves real information of the user. Since the TTP platform returns an authentication result only to the terminal device, which in turn sends the authentication result to a platform server, the platform server cannot acquire the real information of the user, and the user authentication process is anonymous to the platform server. In addition, after the TTP platform authenticates the real information of the user, a first encryption key can be shared between the terminal device and an information providing server, to simplify the complexity of intervention of the TTP platform when the terminal device needs to acquire an electronic file later. Moreover, since the terminal device and the information providing server share the first encryption key that is generated based on login information of the user logging in to the platform server and a first identifier, the first encryption key does not need to be saved on the terminal device, thereby improving the security of the electronic file. Since the user does not need to manually decrypt the encrypted electronic file using the first encryption key, user experience is improved.

Figure 4:
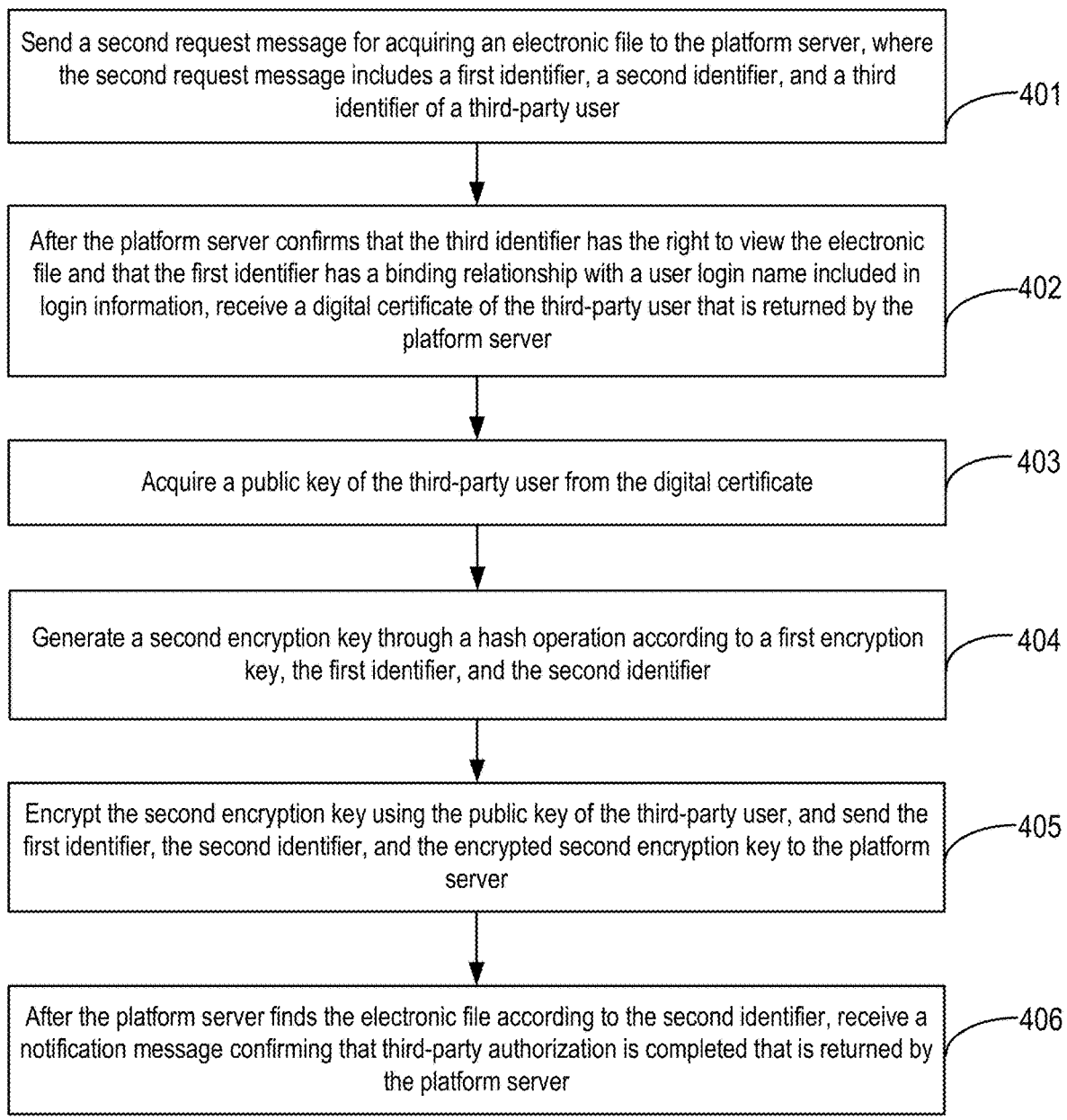
FIG. 4 is a flow diagram illustrating a method for acquiring an electronic file according to some embodiments of the disclosure.

FIG. 4 is a flow diagram of a method for acquiring an electronic file shown according to some embodiments of the disclosure.

On the basis of the embodiment shown in FIG. 1, FIG. 2, or FIG. 3, in this embodiment, when an electronic file is acquired from a platform server using a non-user login name, other participants view the electronic file under the authorization of a user login name (for example, when the electronic file is an electronic prescription, other participants are, for example, pharmacies or other doctors). Since the other participants need to be trusted third parties that register with the platform server and that are approved, the other participants need to have digital certificates, for example, when a pharmacy needs to acquire an electronic prescription from an EPP, this embodiment is exemplarily described using a third-party user (for example, a pharmacy) acquiring an electronic file as an example. As shown in FIG. 4, the method includes the following steps.

Step 401: Send a second request message for acquiring an electronic file to the platform server, where the second request message includes a first identifier, a second identifier, and a third identifier of a third-party user.

Step 402: After the platform server confirms that the third identifier has the right to view the electronic file and that the first identifier has a binding relationship with a user login name included in login information, receive a digital certificate of the third-party user that is returned by the platform server.

Step 403: Acquire a public key of the third-party user from the digital certificate.

Step 404: Generate a second encryption key through a hash operation according to a first encryption key, the first identifier, and the second identifier.

Step 405: Encrypt the second encryption key using the public key of the third-party user, and send the first identifier, the second identifier, and the encrypted second encryption key to the platform server.

Step 406: After the platform server finds the electronic file according to the second identifier, receive a notification message confirming that third-party authorization is completed that is returned by the platform server.

In step 401, a user of a terminal device logs in to the platform server using his user login name. Reference may be made to the description of step 201 to step 203 for the login processes, which will not be described in detail herein. Unlike step 201 to step 203, the second request message includes a third identifier of a third-party user, the platform server obtains the third identifier after parsing the second request message, and the platform server may determine, through the third identifier, that the user login name needs to be authorized to the third-party user for acquiring the electronic file corresponding to the user login name.

In step 402, the platform server confirms whether the third-party user has the right to view the electronic file and determines whether the user login name has a binding relationship with an information providing server, and after determining that the third-party user has the right to view the electronic file and that the user login name has the binding relationship with the information providing server, returns a digital certificate (B_Cert) of the third-party user to the user of the terminal device.

In step 403 and step 404, a public key of the third-party user is determined from the digital certificate of the third-party user, and a digital envelope is generated and a second encryption key KP (those skilled in the art can understand that this embodiment may implement encryption and decryption of an electronic file by means of symmetrical encryption, and therefore an encryption key is the same as a decryption key) corresponding to a prescription is encrypted according to the public key of the third-party user, and the first identifier, the second identifier, and the digital certificate of the third-party user are together sent to the platform server. In one embodiment, the terminal device may generate a first encryption key according to the description of step 101, and generate a second encryption key corresponding to the electronic file based on the first identifier, the second identifier, and the first encryption key.

In step 405 and step 406, the platform server may search for the electronic file according to information such as the second identifier, encrypt the electronic file and the second encryption key using the public key of the third-party user, send the electronic file and the encryption key that are encrypted to a terminal device corresponding to the third-party user, and send a notification message indicating that the authorization is already completed to a login user name of the terminal device, and then the third-party user performs decryption using a private key corresponding to his public key to obtain the second encryption key KP, and further decrypts the electronic file using the second encryption key KP, and finally the validity of the electronic file can be verified through the decrypted electronic file.

In this embodiment, when a user login name sends a second request message, the second request message includes a third identifier of a third-party user, so that a platform server can share an electronic file and a second encryption key of the electronic file with the third-party user by using a digital envelope of the third-party user. Since the flow of reacquiring a key by the third-party user is not needed, the platform server does not obtain any private information concerning the electronic file in the whole process. Further, since the third-party user only has the electronic file of a second identifier, the third-party user cannot infer from the electronic file keys of other electronic files of other user login names on the platform server, and thus cannot obtain more electronic files, thereby sufficiently ensuring the security in the process of acquiring an electronic file.

Figure 5A:
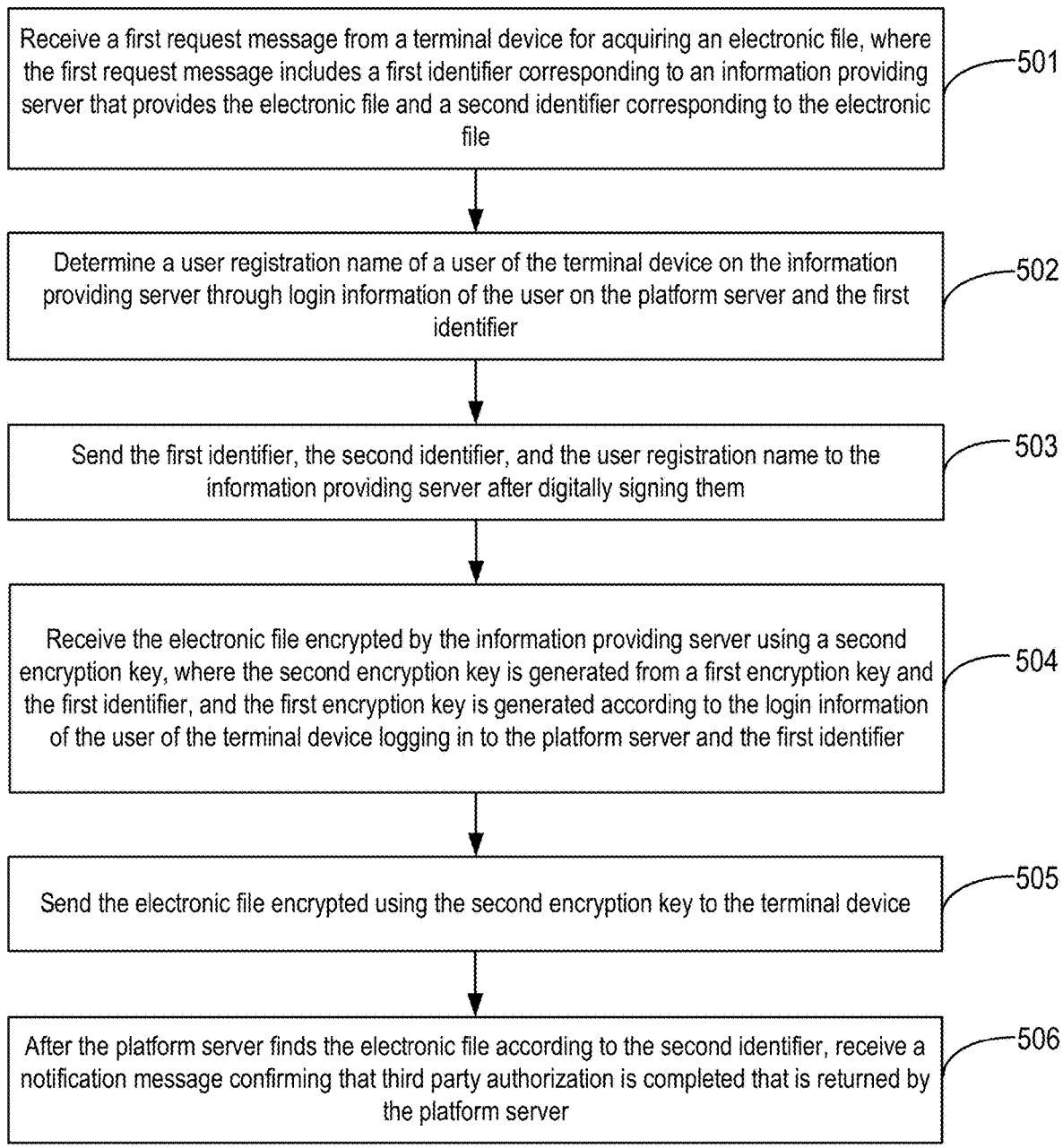
FIG. 5A is a flow diagram illustrating a method for acquiring an electronic file according to some embodiments of the disclosure.

FIG. 5A is a flow diagram illustrating a method for acquiring an electronic file shown according to some embodiments of the disclosure. This embodiment may be executed by a platform server and include the following steps.

Step 501: Receive a first request message from a terminal device for acquiring an electronic file, where the first request message includes a first identifier corresponding to an information providing server that provides the electronic file and a second identifier corresponding to the electronic file.

Step 502: Determine a user registration name of a user of the terminal device on the information providing server through login information of the user on the platform server and the first identifier.

Step 503: Send the first identifier, the second identifier, and the user registration name to the information providing server after digitally signing them.

Step 504: Receive the electronic file encrypted by the information providing server using a second encryption key, where the second encryption key is generated from a first encryption key and the first identifier, and the first encryption key is generated according to the login information of the user of the terminal device logging in to the platform server and the first identifier.

Step 505: Send the electronic file encrypted using the second encryption key to the terminal device.

Step 506: After the platform server finds the electronic file according to the second identifier, receive a notification message confirming that third party authorization is completed that is returned by the platform server.

In step 501, reference is made to the embodiment shown in FIG. 1 for the relevant description of the electronic file, which will not be described in detail in this embodiment. This embodiment is exemplarily described using the electronic file being specifically an electronic prescription as an example. In one embodiment, the first request message may carry the first identifier, and at this time, the first identifier is a hospital code HIS_ID corresponding to a user of a terminal device on an HIS, and the second identifier is a prescription number P_ID of the electronic prescription.

In step 502, in one embodiment, the platform server may establish a binding relationship between a user login name and the first identifier and save the binding relationship. In another embodiment, the platform server may further establish a binding relationship between a user login name in login information and a user registration name of a user corresponding to the user login name on the information providing server, and after the user logs in to the platform server using the user login name, the user registration name corresponding to the user login name on the information providing server of the first identifier can be determined.

In step 504 and step 505, the information providing server may verify the validity of the digital signature, and after the verification is passed, the electronic file is found according to the second identifier, and content to be encrypted in the electronic file is determined. For example, when the electronic file is an electronic prescription, relevant private information concerning a patient in the electronic prescription may be encrypted using a second encryption key. In one embodiment, the second encryption key used for encrypting the electronic file by the information providing server may be generated through a hash operation according to first encryption keys agreed on between the information providing server and different user registration names and the first identifier.

In this embodiment, after an electronic file is encrypted using a second encryption key, a platform server cannot acquire real content of the electronic file. Thus, when any electronic file is sent from an information providing server to the platform server, since the electronic file and a relevant identifier are already encrypted using a second encryption key and the platform server does not have the second encryption key, the platform server cannot leak relevant privacy of the electronic file. Since the second encryption key is generated from login information of a user on the platform server and a first identifier, the user can obtain the second encryption key without the need to exchange the second encryption key with the information providing server, thereby facilitating use by the user.

Figure 5B:
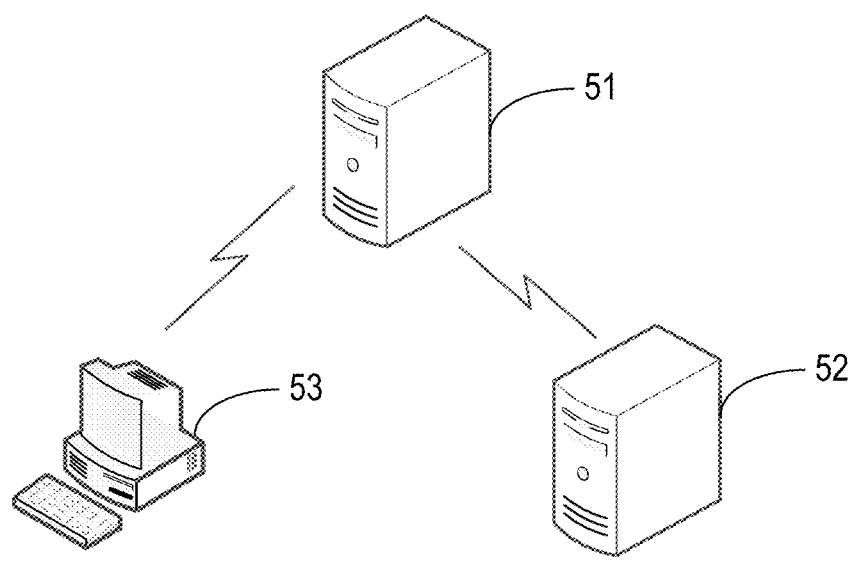
FIG. 5B is a block diagram of a system for acquiring an electronic file according to some embodiments of the disclosure.

FIG. 5B is a block diagram of a system for acquiring an electronic file shown according to some embodiments of the disclosure. As shown in FIG. 5B, as an exemplary scenario, a user login name of a user on a platform server 51 is a mobile phone number "138," a first identifier of an information providing server 52 is "the 309th Hospital," a user registration name on the information providing server 53 is ZHANG San, and the platform server 51 binds 138 to the user registration name "ZHANG San" corresponding to the 309th Hospital. When ZHANG San needs to search for an electronic prescription thereof having a second identifier "123" in the 309th Hospital, ZHANG San logs in to the platform server 51 using the user login name "138" and a corresponding login password through a terminal device 53, and sends a first request message to the platform server 51. Upon receiving the first request message, the platform server 51 determines that the corresponding hospital is the 309th Hospital through 138, and then sends 309, 123, and ZHANG San to the information providing server 52 corresponding to the 309th Hospital after digitally signing them, and the information providing server 52 determines the electronic prescription having the second identifier of 123 through the aforementioned information. The platform server 51 receives the electronic file encrypted by the information providing server 52 using a second encryption key, and sends the electronic file encrypted using the second encryption key to the terminal device 53.

Figure 5C:
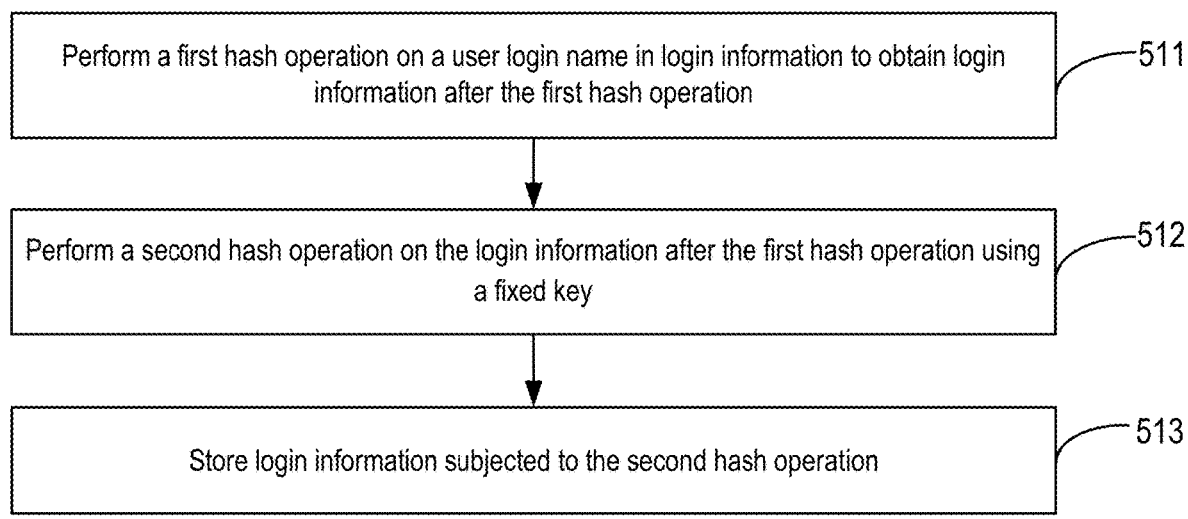
FIG. 5C is a flow diagram illustrating a method performed by a platform server for storing login information of a user shown according to some embodiments of the disclosure.

FIG. 5C is a flow diagram illustrating a method performed by a platform server for storing login information of a user shown according to some embodiments of the disclosure. As shown in FIG. 5C, when a user of a terminal device needs to register with the platform server, how the platform server stores login information of the user includes the following steps.

Step 511: Perform a first hash operation on a user login name in login information to obtain login information after the first hash operation.

Step 512: Perform a second hash operation on the login information after the first hash operation using a fixed key.

Step 513: Store login information subjected to the second hash operation.

In step 511 to step 513, in one embodiment, a mobile phone number may be used as a user registration name, and a user login name of a user on the platform server follows the principle of being capable of identifying the identity of the user, so the platform server only needs to save the mobile phone number of the user and a login password. A mobile phone number is personal identification information according to requirements of the HIPAA, so data needs to be desensitized before being saved in this embodiment.

In one embodiment, a hash operation may be performed on the user login name, and then a hash operation is performed again on the user login name and a fixed key saved by the platform server, that is, Hash (Hash (User_Phone), Seed_EPP), and the login password of the user may be saved by means of "login password+fixed key+Salt" and then hashing, that is, Hash (User_Passwd, Seed_EPP, Salt), where Salt is a random number.

Thus, the information relevant to the user information and the user login name stored by the platform server may be represented as Table 1.

TABLE 1

| User_ID | Passwd | Salt | ... |
|---|---|---|---|
| Hash (Hash (User_Phone), Seed_EPP) | Hash (User_Passwd, Seed_EPP, Salt) | Random number | ... |

After the processing above is performed on login information of a user, it can be ensured that an attacker cannot infer the login information of the user. Since a random variable Salt is added when a hash operation is performed, even if the attacker acquires the login information of the user stored by a platform server, the attacker cannot obtain a fixed key Seed_EPP, and therefore the attacker cannot reversely infer a user login name in the login information through a hash operation. Moreover, since the fixed key is a random variable randomly generated on the platform server side and has a small data length, a layer of protection is added to the login information of the user stored on the platform server by introducing the fixed key Seed_EPP in this embodiment.

Figure 6:
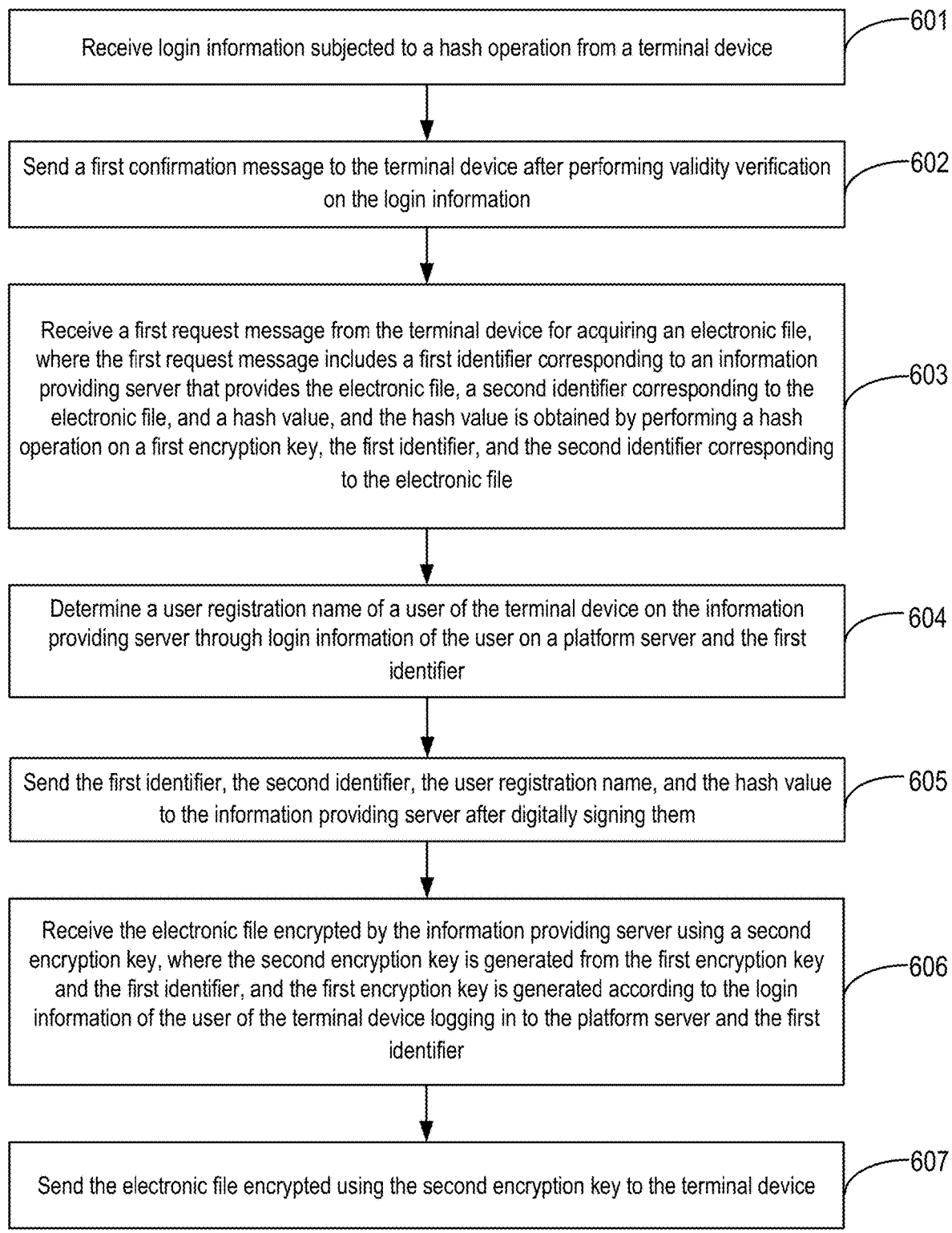
FIG. 6 is a flow diagram illustrating a method for acquiring an electronic file according to some embodiments of the disclosure.

FIG. 6 is a flow diagram illustrating a method for acquiring an electronic file shown according to some embodiments of the disclosure.

Step 601: Receive login information subjected to a hash operation from a terminal device.

Step 602: Send a first confirmation message to the terminal device after performing validity verification on the login information.

Step 603: Receive a first request message from the terminal device for acquiring an electronic file, where the first request message includes a first identifier corresponding to an information providing server that provides the electronic file, a second identifier corresponding to the electronic file, and a hash value, and the hash value is obtained by performing a hash operation on a first encryption key, the first identifier, and the second identifier corresponding to the electronic file.

Step 604: Determine a user registration name of a user of the terminal device on the information providing server through login information of the user on a platform server and the first identifier.

Step 605: Send the first identifier, the second identifier, the user registration name, and the hash value to the information providing server after digitally signing them.

Step 606: Receive the electronic file encrypted by the information providing server using a second encryption key, where the second encryption key is generated from the first encryption key and the first identifier, and the first encryption key is generated according to the login information of the user of the terminal device logging in to the platform server and the first identifier.

Step 607: Send the electronic file encrypted using the second encryption key to the terminal device.

In step 601 to step 602, in one embodiment, a user login name (which may also be referred to as a user identifier) included in the login information may be a mobile phone number of the user, and the terminal device may perform a hash operation on the mobile phone number, so that the platform server cannot acquire real login information of the real user of the terminal device when the user logs in to the platform server using the user login name after the hash operation, thereby preventing an eavesdropper from stealing the login information of the user of the terminal device and the platform server from leaking the login information of the user of the terminal device.

Reference is made to the embodiment shown in FIG. 5A for the description of step 603 to step 607, which will not be described in detail herein.

In this embodiment, on the basis of the beneficial technical effects of the aforementioned embodiment, since a hash operation is already performed on login information by a terminal device, the platform server cannot acquire real login information of a user of the terminal device, thereby preventing an eavesdropper from stealing the login information of the user of the terminal device and the platform server from leaking the login information of the user of the terminal device; a hash value is used, so that an information providing server can verify the validity of this first request message.

Figure 7:
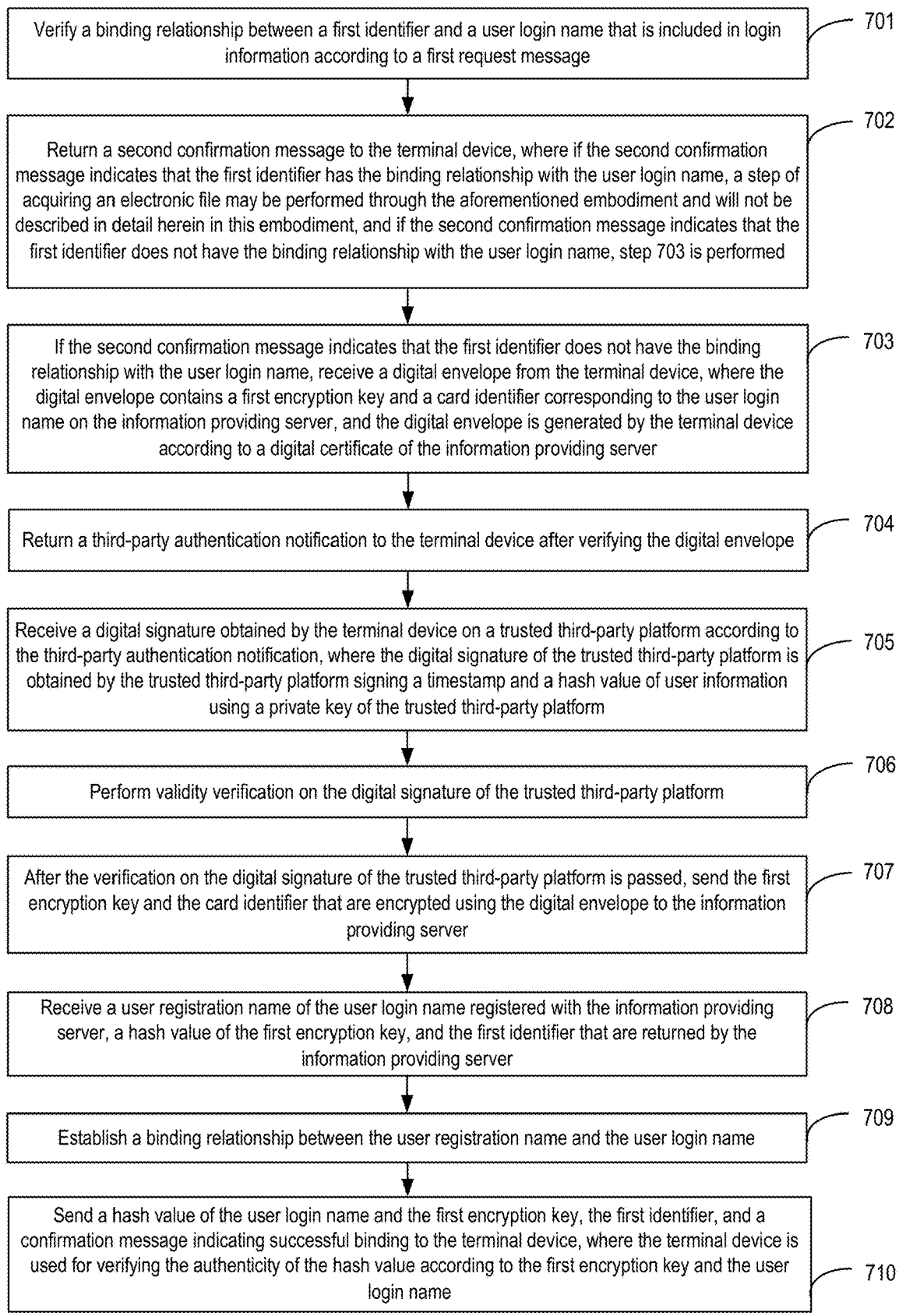
FIG. 7 is a flow diagram illustrating a method for acquiring an electronic file according to some embodiments of the disclosure.

FIG. 7 is a flow diagram illustrating a method for acquiring an electronic file according to some embodiments of the disclosure. On the basis of the embodiment shown in FIG. 5A or FIG. 6, this embodiment is exemplarily described using a user login name needing to be bound to an information providing server and authorization and authentication in the process of acquiring an electronic prescription as an example. A user of a terminal device already registers with a platform server and has his corresponding user login name, and the user of the terminal device also registers with a TTP platform, and the user of the terminal device already logs in to the platform server. As shown in FIG. 7, the method includes the following steps:

Step 701: Verify a binding relationship between a first identifier and a user login name that is included in login information according to a first request message.

Step 702: Return a second confirmation message to the terminal device, where if the second confirmation message indicates that the first identifier has the binding relationship with the user login name, a step of acquiring an electronic file may be performed through the aforementioned embodiment and will not be described in detail herein in this embodiment, and if the second confirmation message indicates that the first identifier does not have the binding relationship with the user login name, step 703 is performed.

Step 703: If the second confirmation message indicates that the first identifier does not have the binding relationship with the user login name, receive a digital envelope from the terminal device, where the digital envelope contains a first encryption key and a card identifier corresponding to the user login name on the information providing server, and the digital envelope is generated by the terminal device according to a digital certificate of the information providing server.

Step 704: Return a third-party authentication notification to the terminal device after verifying the digital envelope.

Step 705: Receive a digital signature obtained by the terminal device on a trusted third-party platform according to the third-party authentication notification, where the digital signature of the trusted third-party platform is obtained by the trusted third-party platform signing a timestamp and a hash value of user information using a private key of the trusted third-party platform.

Step 706: Perform validity verification on the digital signature of the trusted third-party platform.

Step 707: After the verification on the digital signature of the trusted third-party platform is passed, send the first encryption key and the card identifier that are encrypted using the digital envelope to the information providing server.

Step 708: Receive a user registration name of the user login name registered with the information providing server, a hash value of the first encryption key, and the first identifier that are returned by the information providing server.

Step 709: Establish a binding relationship between the user registration name and the user login name.

Step 710: Send a hash value of the user login name and the first encryption key, the first identifier, and a confirmation message indicating successful binding to the terminal device, where the terminal device is used for verifying the authenticity of the hash value according to the first encryption key and the user login name.

In this embodiment, a user is authenticated secondarily through a TTP platform, and then an information providing server compares a real user corresponding to a user login name with a user registration name already registered with the information providing server, thereby preventing a malicious user from stealing information of a valid user for binding to the information providing server. Since a platform server does not read any real information concerning the user in the whole binding process, the platform server only serves as a proxy channel to assist in binding between a user of a terminal device and the information providing server, so as to effectively realize privacy protection of the user; in addition, since the information providing server and the user of the terminal device share a first encryption key, later secondary authentication for acquiring an electronic file may be aided, so as to reduce the complexity of subsequent operations. In addition, during authentication by the TTP, since a timestamp is added into the TTP, a malicious user can be prevented from attacking a valid user in other scenarios requiring secondary authentication (for example, the user of the terminal device needs to reset his login password on the platform server) after the malicious user detects the authentication information.

Figure 8:
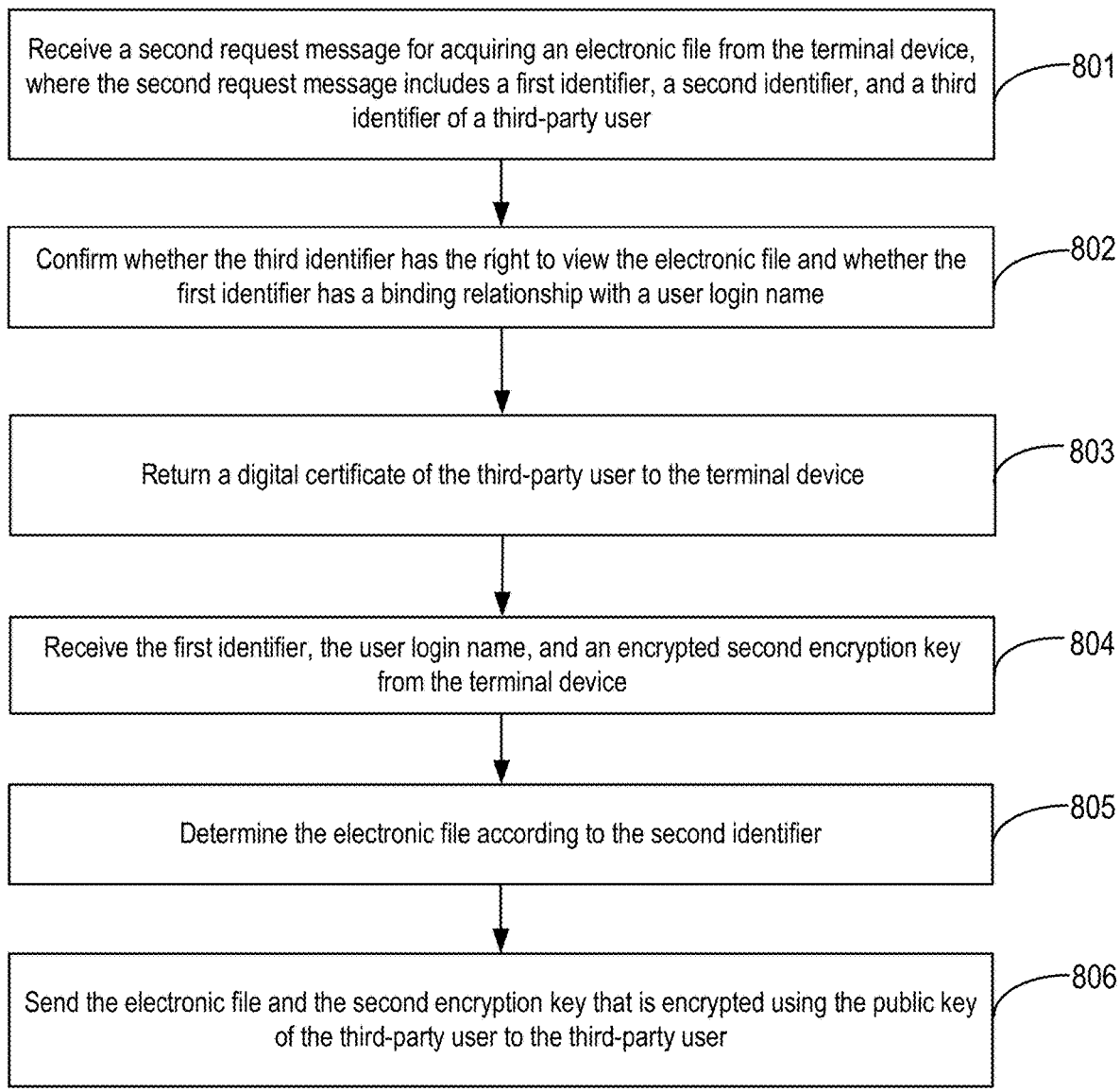
FIG. 8 is a flow diagram illustrating a method for acquiring an electronic file according to some embodiments of the disclosure.

FIG. 8 is a flow diagram illustrating a method for acquiring an electronic file according to some embodiments of the disclosure. On the basis of the embodiment shown in FIG. 5A, FIG. 6, or FIG. 7, in this embodiment, when an electronic file is acquired from a platform server using a non-user login name, other participants view the electronic file under the authorization of a user login name (for example, when the electronic file is an electronic prescription, other participants are, for example, pharmacies or other doctors). Since the other participants need to be trusted third parties that register with the platform server and that are approved, the other participants need to have digital certificates, for example, when a pharmacy needs to acquire an electronic prescription from an EPP, this embodiment is exemplarily described using a third-party user (for example, a pharmacy) acquiring an electronic file as an example. As shown in FIG. 8, the method includes the following steps.

Step 801: Receive a second request message for acquiring an electronic file from the terminal device, where the second request message includes a first identifier, a second identifier, and a third identifier of a third-party user.

Step 802: Confirm whether the third identifier has the right to view the electronic file and whether the first identifier has a binding relationship with a user login name, and perform step 803 after confirming that the third identifier has the right to view the electronic file and that the first identifier has the binding relationship with the user login name.

Step 803: Return a digital certificate of the third-party user to the terminal device.

Step 804: Receive the first identifier, the user login name, and an encrypted second encryption key from the terminal device, where the second encryption key is generated through a hash operation according to a first encryption key, the first identifier, and the user login name and encrypted using a public key in the digital certificate of the third-party user.

Step 805: Determine the electronic file according to the second identifier.

Step 806: Send the electronic file and the second encryption key that is encrypted using the public key of the third-party user to the third-party user, where a terminal of the third-party user decrypts, according to a private key of the third-party user, the second encryption key encrypted using the public key of the third-party user, so as to obtain the second encryption key, and decrypts private information in the electronic file according to the second encryption key.

In step 801, a user of the terminal device logs in to the platform server using his user login name. Reference may be made to the description of step 601 to step 603 for the login manner, which will not be described in detail herein. Unlike step 601 to step 603, the second request message includes a third identifier of a third-party user, the platform server obtains the third identifier after parsing the second request message, and the platform server may determine, through the third identifier, that the user login name needs to be authorized to the third-party user for acquiring the electronic file corresponding to the user login name.

In step 802 and step 803, the platform server confirms whether the third-party user has the right to view the electronic file and determines whether the user login name has a binding relationship with an information providing server, and after determining that the third-party user has the right to view the electronic file and that the user login name has the binding relationship with the information providing server, returns a digital certificate (B_Cert) of the third-party user to the user of the terminal device.

In step 804, a public key of the third-party user is determined from the digital certificate of the third-party user, and a digital envelope is generated and a second encryption key KP (those skilled in the art can understand that this embodiment may implement encryption and decryption of an electronic file by means of symmetrical encryption, and therefore an encryption key is the same as a decryption key) corresponding to a prescription is encrypted according to the public key of the third-party user, and the first identifier, the second identifier, and the digital certificate of the third-party user are together sent to the platform server; in one embodiment, the terminal device may generate a first encryption key according to the description of step 101, and generate a second encryption key corresponding to the electronic file based on the first identifier, the second identifier, and the first encryption key.

In step 805 and step 806, in one embodiment, the platform server may send information such as the second identifier to the information providing server, the information providing server searches for the electronic file according to the second identifier, and returns the electronic file and the second encryption key to the platform server after encrypting them using the public key of the third-party user, the platform server sends the electronic file and the second encryption key that are encrypted to a terminal corresponding to the third-party user, and sends a notification message indicating that the authorization is already completed to a login user name of the terminal device, and then the third-party user performs decryption using a private key corresponding to his public key to obtain the second encryption key KP, and further decrypts the electronic file using the second encryption key KP, and finally the validity of the electronic file can be verified through the decrypted electronic file.

In this embodiment, a third identifier of a third-party user is obtained by parsing a second request message, so that a platform server can share an electronic file and a second encryption key of the electronic file with the third-party user by using a digital envelope of the third-party user. Since the flow of reacquiring a key by the third-party user is not needed, the platform server does not obtain any private information concerning the electronic file in the whole process. Since the third-party user only has the electronic file of a second identifier, the third-party user cannot infer from the electronic file keys of other electronic files of other user login names on the platform server, and thus cannot obtain more electronic files, thereby sufficiently ensuring the security in the process of acquiring an electronic file.

Figure 9:
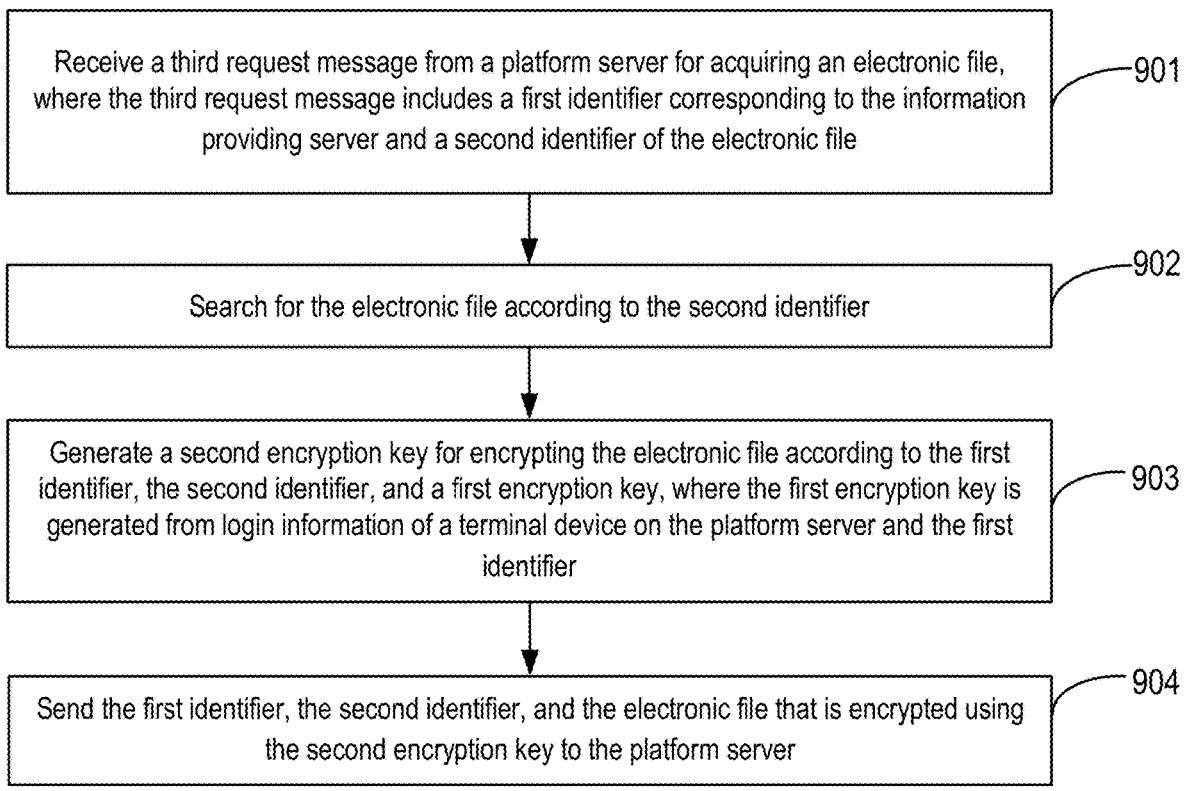
FIG. 9 is a flow diagram illustrating a method for acquiring an electronic file according to some embodiments of the disclosure.

FIG. 9 is a flow diagram illustrating a method for acquiring an electronic file according to some embodiments of the disclosure. The method may be executed by an information providing server and include the following steps.

Step 901: Receive a third request message from a platform server for acquiring an electronic file, where the third request message includes a first identifier corresponding to the information providing server and a second identifier of the electronic file.

Step 902: Search for the electronic file according to the second identifier.

Step 903: Generate a second encryption key for encrypting the electronic file according to the first identifier, the second identifier, and a first encryption key, where the first encryption key is generated from login information of a terminal device on the platform server and the first identifier.

Step 904: Send the first identifier, the second identifier, and the electronic file that is encrypted using the second encryption key to the platform server.

In step 901, reference is made to the embodiment shown in FIG. 1 for the relevant description of the electronic file, which will not be described in detail in this embodiment. This embodiment is exemplarily described using the electronic file being specifically an electronic prescription as an example. In one embodiment, the third request message may carry the first identifier, and at this time, the first identifier is a hospital code HIS_ID corresponding to a user of the terminal device on an HIS, and the second identifier is a prescription number P_ID of the electronic prescription.

In step 903, in one embodiment, when the information providing server encrypts the electronic file, a second encryption key may be generated through a hash operation according to first encryption keys agreed on between the information providing server and different user registration names and the first identifier.

In this embodiment, after an electronic file is encrypted using a second encryption key, a platform server cannot acquire real content of the electronic file. Thus, when any electronic file is sent from an information providing server to the platform server, since the electronic file and a relevant identifier are already encrypted using a second encryption key and the platform server does not have the second encryption key, the platform server cannot leak relevant privacy of the electronic file. Since the second encryption key is generated from login information of a user on the platform server and a first identifier, the user can obtain the second encryption key without the need to exchange the second encryption key with the information providing server, thereby facilitating use by the user.

Figure 10:
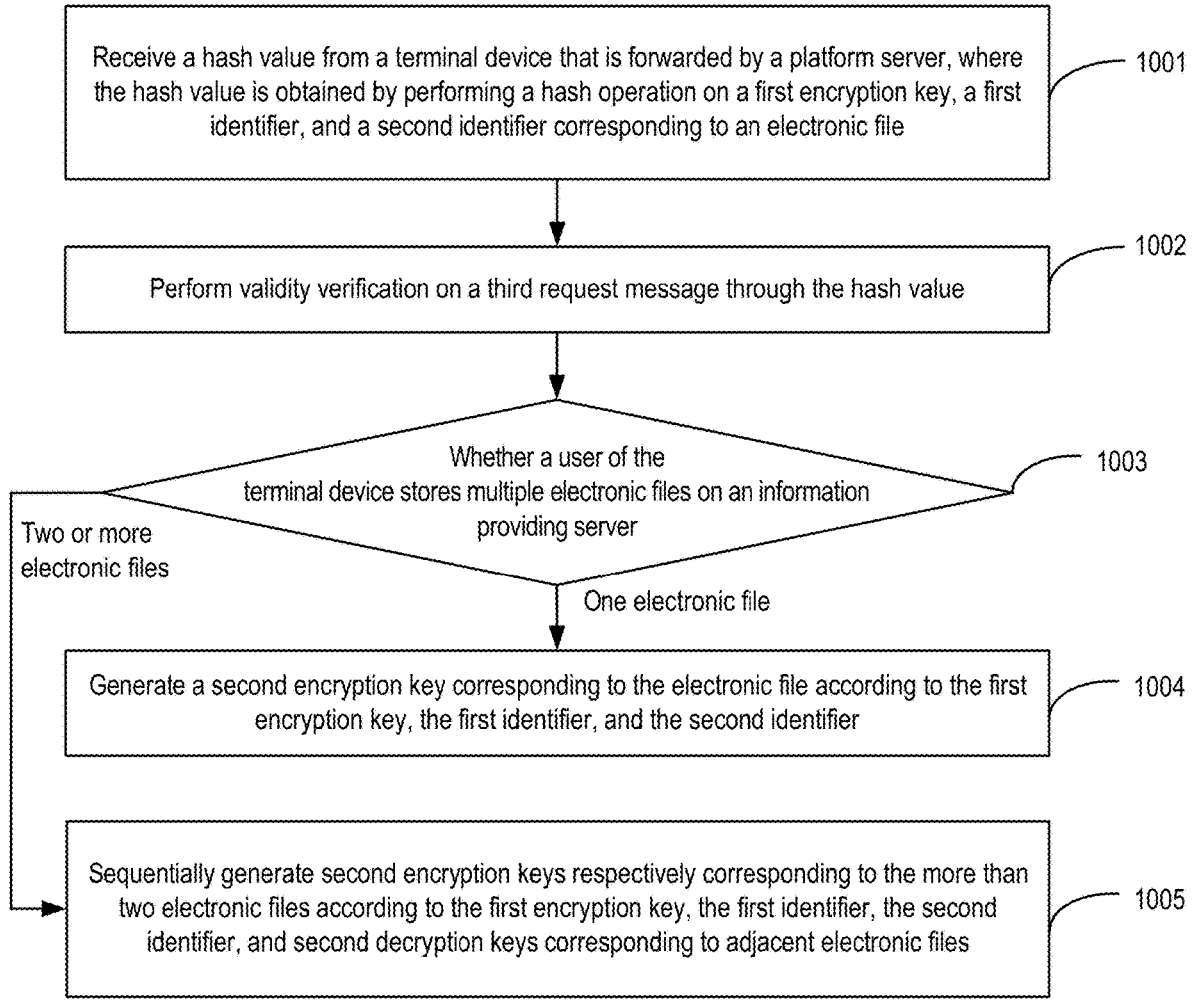
FIG. 10 is a flow diagram illustrating a method for acquiring an electronic file according to some embodiments of the disclosure.

FIG. 10 is a flow diagram illustrating a method for acquiring an electronic file according to some embodiments of the disclosure. On the basis of the embodiment shown in FIG. 9, exemplary description is made using how to verify the validity of the third request message and how to generate the second encryption key as an example. As shown in FIG. 10, the method includes the following steps.

Step 1001: Receive a hash value from a terminal device that is forwarded by a platform server, where the hash value is obtained by performing a hash operation on a first encryption key, a first identifier, and a second identifier corresponding to an electronic file.

Step 1002: Perform validity verification on a third request message through the hash value.

Step 1003: After the validity verification on the third request message is passed, determine whether a user of the terminal device stores multiple electronic files on an information providing server, if one electronic file is stored, perform step 1004, and if two or more electronic files are stored, perform step 1005.

Step 1004: If one electronic file is stored, generate a second encryption key corresponding to the electronic file according to the first encryption key, the first identifier, and the second identifier.

Step 1005: If two or more electronic files are stored, sequentially generate second encryption keys respectively corresponding to the two or more electronic files according to the first encryption key, the first identifier, the second identifier, and second decryption keys corresponding to adjacent electronic files.

In step 1001 and step 1002, validity verification is performed on the third request message, so as to prevent an eavesdropper from stealing an electronic file of a user of the terminal device through an invalid third request message, thereby ensuring the security of the electronic file.

In step 1003 to step 1005, an exemplary description is made using the electronic file being an electronic prescription as an example. Since an electronic prescription needs to flow among multiple roles such as a user, a doctor, and a pharmacy, each electronic prescription of the same user needs to be encrypted using a different key, so as to prevent one of the roles acquiring an encryption key of one electronic prescription of the user from decrypting other electronic prescriptions of the user. Moreover, in some scenarios, the user downloads electronic prescriptions in bulk from the platform server for view. In this situation, all electronic prescriptions need to be decrypted if the same encryption key is employed for them, which involves a large amount of calculation. Given the computing power of a mobile terminal, the complexity in acquiring decryption keys can be effectively reduced during bulk decryption of electronic prescriptions in this embodiment. The specific method is as follows:

When the information providing server encrypts data of electronic files, for the same patient-user, a second encryption key of a first electronic prescription of the patient-user is denoted as KP1, and KP1 is generated by hashing a first encryption key Seed and a first identifier HIS_ID, that is:

$KP1=\text{Hash}(HIS\_ID,\text{Seed})$.

A second encryption key of a second electronic prescription is denoted as KP2 which is generated from KP1, Seed, and HIS_ID, that is:

$KP2=\text{Hash}(HIS\_ID,KP1,\text{Seed})$;

Similarly, a second encryption key KP3 of a third electronic prescription may further be generated till KPn, that is:

$KP3=\text{Hash}(HIS\_ID,KP2,\text{Seed})$;

. . .

$KPn=\text{Hash}(HIS\_ID,KPn-1,\text{Seed})$, where n is the number of electronic prescriptions of the patent.

By means of the aforementioned key generation method, when a user decrypts electronic prescriptions in bulk, it is not needed to share a large number of secret-state prescription encryption keys through a platform server. Since the patient-user can generate Seed through a password, a series of encryption keys can be deduced through simple hash operations, and then decryption is performed, thereby reducing the overhead of decryption to obtain keys. The prescriptions are decrypted sequentially in bulk, so that whether any prescription is lost can be checked, that is, the loss of an electronic prescription in the middle can be found through a mismatch between a decryption key and a prescription, thereby improving the ability to audit an electronic prescription. When it is needed to share an electronic prescription with a third-party user for view, the patient-user can directly deduce a second encryption key of the electronic prescription locally and then encrypt the second encryption key using a public key of the third-party user to realize sharing between the patient-user and the third-party user, thereby avoiding interaction with an information providing server. Moreover, a terminal device does not need to save the second encryption key, thereby simplifying the key sharing flow.

Figure 11:
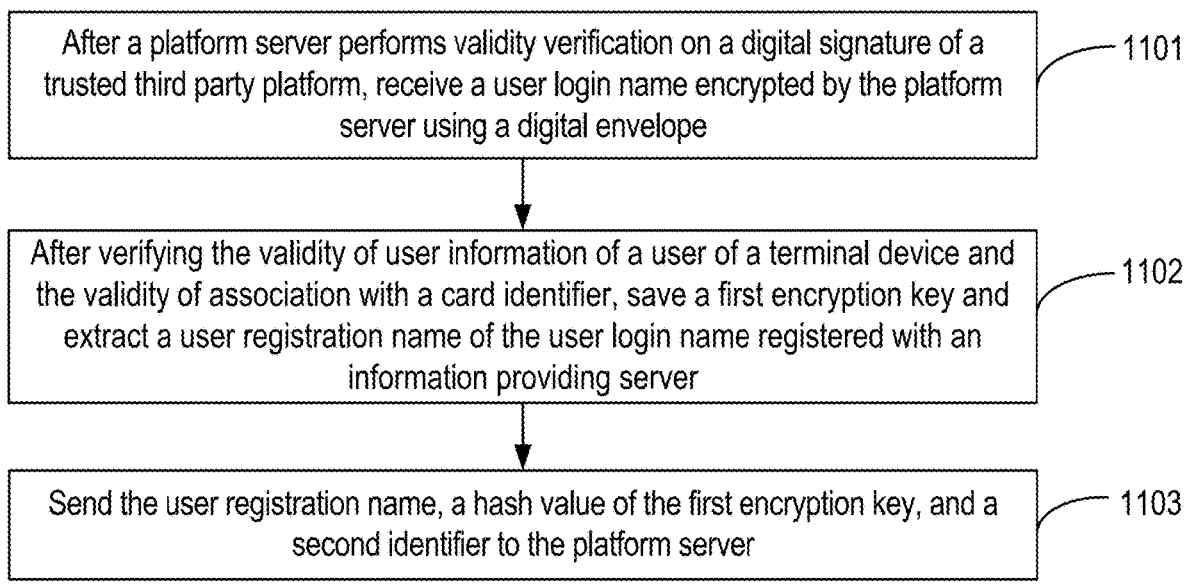
FIG. 11 is a flow diagram illustrating a method for acquiring an electronic file according to some embodiments of the disclosure.

FIG. 11 is a flow diagram illustrating a method for acquiring an electronic file according to some embodiments of the disclosure. The method includes the following steps.

Step 1101: After a platform server performs validity verification on a digital signature of a trusted third-party platform, receive a user login name encrypted by the platform server using a digital envelope, where the digital envelope is generated by a terminal device from a card identifier of a user on an information providing server using a digital certificate corresponding to the information providing server.

Step 1102: After verifying the validity of user information of the user of the terminal device and the validity of association with the card identifier, save a first encryption key and extract a user registration name of the user login name registered with the information providing server.

Step 1103: Send the user registration name, a hash value of the first encryption key, and a second identifier to the platform server.

In this embodiment, an information providing server compares a real user with a user registration name already registered with the information providing server, thereby preventing a malicious user from stealing information of a valid user for binding to the information providing server. Moreover, a platform server does not read any real information concerning the user in the whole binding process, and the platform server only serves as a proxy channel to assist in binding between a user and the information providing server through a terminal device, so that privacy protection of the user can be effectively realized. Finally, the information providing server and the user share a first encryption key, so that later secondary authentication for acquiring an electronic file can be aided, thereby reducing the complexity of subsequent operations.

Figure 12:
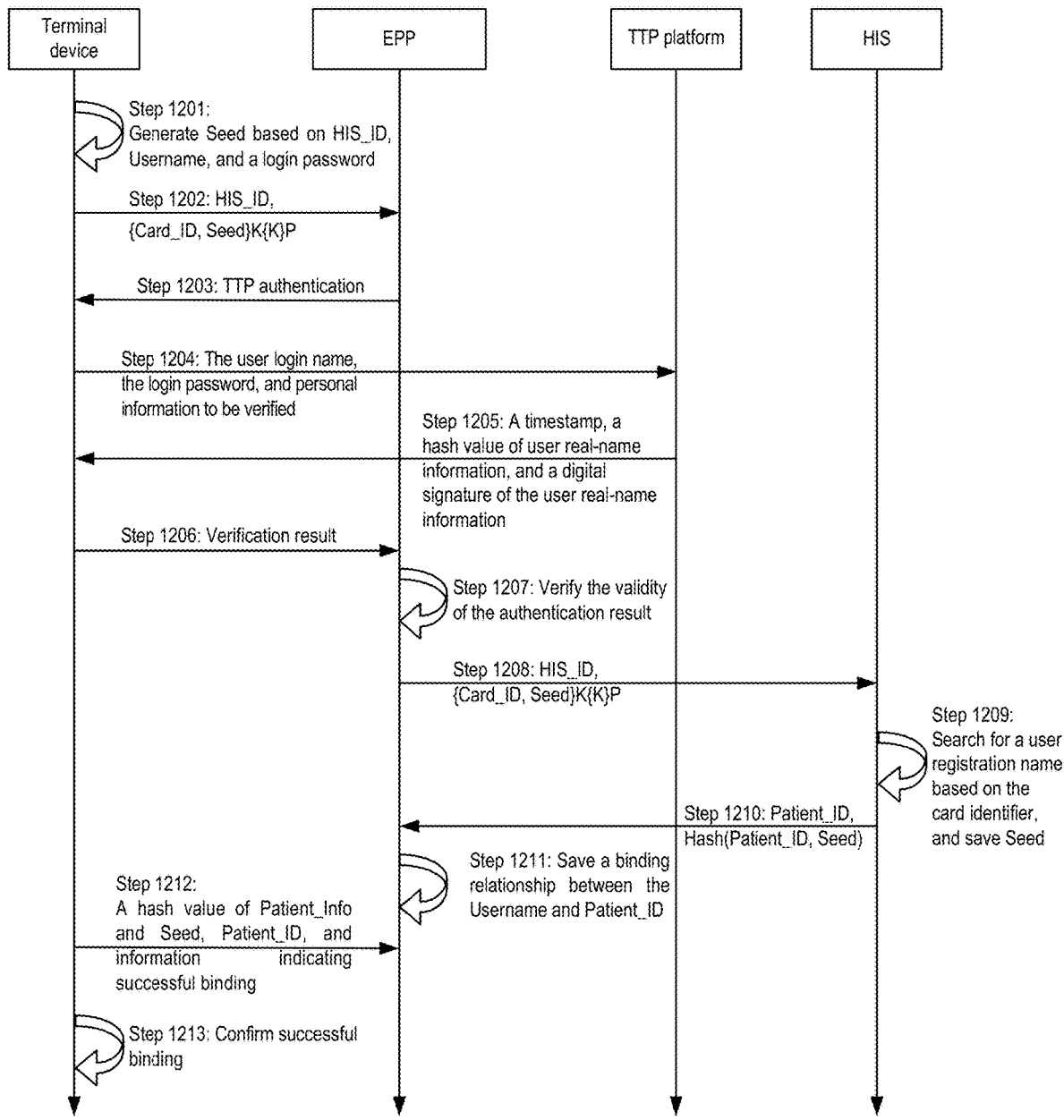
FIG. 12 is an activity diagram of a method for acquiring an electronic file according to some embodiments of the disclosure.

FIG. 12 is an activity diagram of a method for acquiring an electronic file according to some embodiments of the disclosure. This embodiment uses an electronic file being an electronic prescription, a platform server being an EPP, and an information providing server being an HIS as an example, and a user of a terminal device already becoming a registered user of the EPP (corresponding to a user login name) and a registered user of the HIS (corresponding to a user registration name) to describe how to bind the user login name of the user on the EPP to the user registration name on the HIS.

As shown in FIG. 12, the method includes the following steps.

Step 1201: The terminal device generates a first encryption key Seed based on a first identifier (HIS_ID), a user login name (Username), and a login password. In this embodiment, Seed may be shared between the user and the HIS, so that the HIS uses Seed in multiple later encryption protection flows. In one embodiment, Seed may be generated based on a user login name and a login password of the user on the EPP platform, and a first identifier HIS_ID. In one embodiment, the method for generating Seed may be:

$\text{Seed}=\text{Hash}(HIS\_ID,\text{Username},\text{Password})$.

In this embodiment, since Seed is generated using the user login name and the login password that are known to the user and the first identifier HIS_ID known on the EPP side together, a client does not need to save the Seed, thereby avoiding information leakage caused by attack or due to loss of the client. Moreover, the EPP platform saves the login password (Password) subjected to a hash operation, the EPP cannot deduce Seed, to ensure that Seed is shared only between the user and the HIS. Similarly, the HIS also cannot infer from Seed the login password of the user on the EPP and a hash value of the login password, so the security of the login password of the user is not affected. Since the user does not need to memorize more relevant password information and the terminal device does not need to store Seed, the user does not need to perform an operation of exporting Seed from the terminal device, destroying Seed in the terminal device or the like when replacing the terminal device, thereby improving user experience.

Step 1202: The terminal device requests the EPP for binding to a corresponding HIS based on HIS_ID, and sends information required by the HIS such as the generated Seed and a card identifier (Card_ID) to the EPP after encrypting the information using a digital envelope generated through a digital certificate that is provided by the HIS; in one embodiment, the digital envelope is generated using the digital certificate, and a formula of the digital envelope may be represented as {Msg}K{K}P, where P is a public key (which may also be referred to as a digital certificate) of the HIS, K is a random key, P and K are combined to provide a protection method to protect Msg, and in this embodiment, Msg is Seed and the card identifier.

Step 1203: The EPP requires the user to perform secondary authentication with a TTP platform after auditing information such as HIS_ID, Seed, and the card identifier (Card_ID).

Step 1204: The terminal device provides the user login name, the login password, and personal information (Patient_Info) in an electronic prescription to be verified to the TTP platform based on a trusted third-party HTTPS connection, where the personal information is, for example, an identity card number, a mobile phone number, or a social security card number of the user.

Step 1205: The TTP platform sends a timestamp, a hash value of user real-name information, and a digital signature of the user real-name information to the user after verifying the user login name, the login password, and the personal information in the electronic prescription.

Step 1206: The terminal device sends a verification result to the EPP.

Step 1207: The EPP verifies the validity of the verification result of the TTP platform.

Step 1208: The EPP sends the encrypted user information in step 1202 to the HIS. In this embodiment, the encrypted information in step 1202 is the information required by the HIS such as Seed and the card identifier (Card_ID).

Step 1209: After verifying the validity of the user information and the validity of association with the card identifier, the HIS saves Seed and extracts a user registration name Patient_ID registered by the user with the HIS.

Step 1210: The HIS sends a hash value of the user registration name and Seed, and the user registration name together to the EPP.

Step 1211: The EPP establishes a binding relationship between the user login name of the EPP and the user registration name Patient_ID according to information returned by the HIS, and saves the binding relationship.

Step 1212: The EPP forwards a hash value of Patient_Info and Seed, Patient_ID, and information indicating successful binding to the terminal device.

Step 1213: The terminal device calculates the authenticity of the hash value using Seed and Patient_Info, and confirms successful binding.

In the aforementioned binding process of this embodiment, a third-party authentication platform authenticates a user secondarily, and then a hospital compares a real user and personal information already registered with an HIS, thereby preventing a malicious user from stealing information of others for binding to the hospital. Since an EPP only serves as a proxy channel to assist in binding between a user and the HIS in the whole binding process, the EPP platform does not read any real information concerning the user, so that privacy protection of the user can be effectively realized. Finally, the HIS and the user share Seed, so that later secondary authentication for acquiring a prescription can be aided, thereby reducing the complexity of subsequent operations. It should be noted that when the trusted third-party performs authentication, a timestamp is added, so that a malicious user can be prevented from detecting the current authentication information, thereby preventing the malicious user from replay attack in other scenarios requiring secondary authentication (for example, the user modifies the login password or the like).

Figure 13:
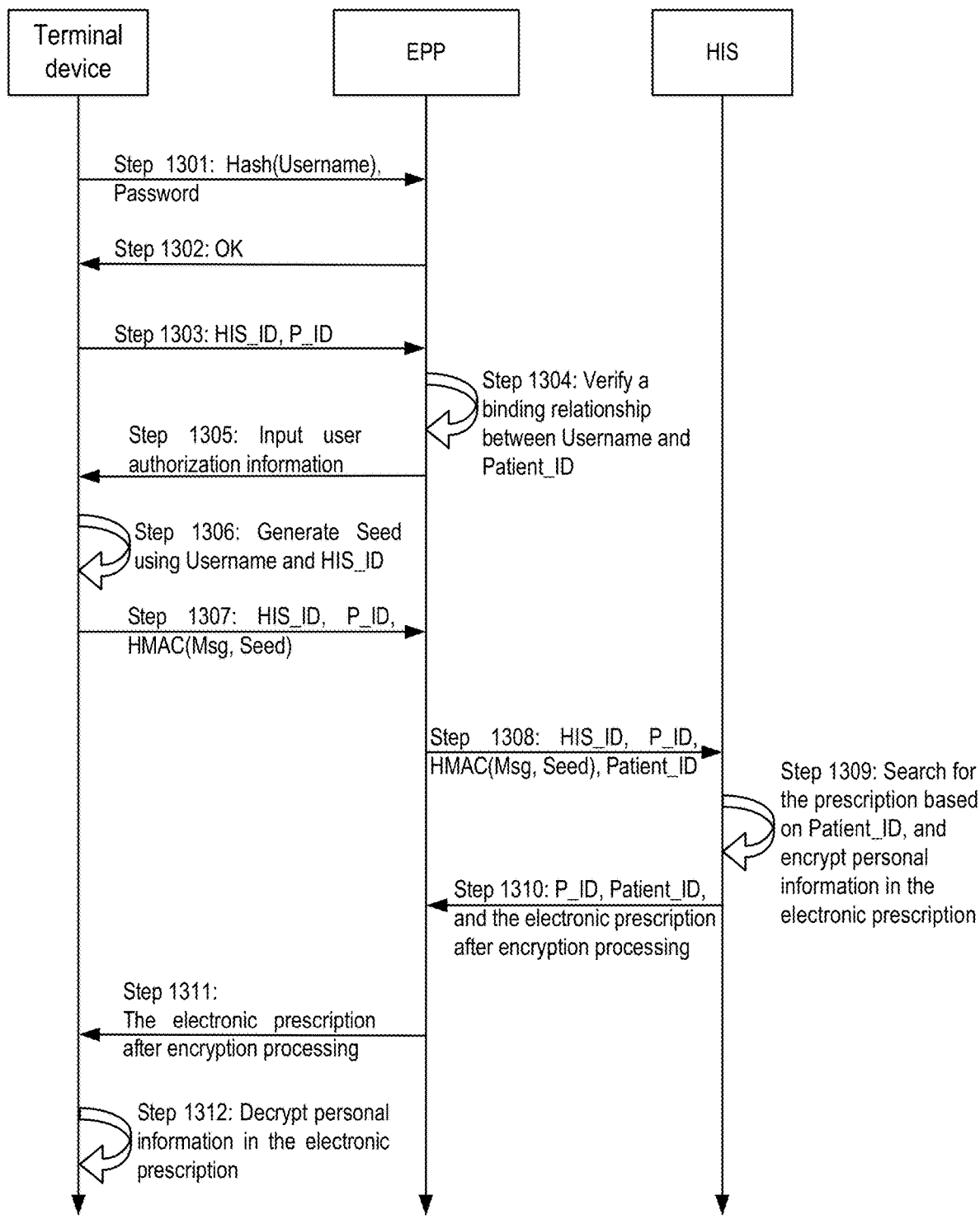
FIG. 13 is an activity diagram of a method for acquiring an electronic file according to some embodiments of the disclosure.

FIG. 13 is an activity diagram of a method for acquiring an electronic file according to some embodiments of the disclosure. This embodiment is exemplarily described using an electronic file being an electronic prescription, a platform server being an EPP, and an information providing server being an HIS as an example. In the situation that a user login name is already bound to a user registration name of a user on the HIS, the user may apply for a personal electronic prescription on the relevant HIS from the EPP through a terminal device. As shown in FIG. 13, the method includes the following steps.

Step 1301: The user logs in to the EPP using a hash value of a mobile phone number and a login password through the terminal device.

Step 1302: The EPP returns confirmation information indicating successful login after performing verification.

Step 1303: The terminal device sends a first request message to the EPP to request acquisition of an electronic prescription, where the first request message includes a first identifier HIS_ID and a prescription number P_ID.

Step 1304: The EPP verifies a binding relationship between a user login name and a user registration name of the user on the HIS, and verifies whether the electronic prescription exists, if the electronic prescription exists, performs step 1311, and if the electronic prescription does not exist, performs step 1305.

Step 1305: The EPP provides a feedback requiring input of user authorization information.

Step 1306: The terminal device generates Seed using login information and the first identifier.

Step 1307: The terminal device sends the first identifier HIS_ID corresponding to the HIS, a second identifier P_ID of the electronic prescription, and the like together to the EPP, where a hash-based message authentication code (HMAC for short) is performed on the whole message using Seed shared by the HIS and the user.

Step 1308: The EPP forwards data in step 1307 and the user registration name Patient_ID to the HIS after signing them.

Step 1309: The HIS verifies the validity of this request of the user using the HMAC and the signature of the EPP, searches for the prescription based on Patient_ID, and generates a second encryption key KP to encrypt personal information in the electronic prescription.

Step 1310: The HIS sends the second number P_ID, the user registration name Patient_ID, the prescription after encryption processing, and a corresponding HIS signature to the EPP.

Step 1311: After obtaining authorization, the EPP sends information such as the electronic prescription to the terminal device after signing the information.

Step 1312: The terminal device generates a decryption key using Seed, decrypts the personal information in the electronic prescription, and then verifies the validity of the electronic prescription through the personal information.

In the aforementioned process, the HIS realizes authentication of a user using Seed pre-shared with the user, and the HIS realizes integrity verification on authorization information by means of HMAC, so as to obtain real authorization of a valid user for acquiring a prescription, and the EPP does not obtain any personal private information in the process. Moreover, each prescription uses a different key, so as to prevent leakage of more information when a prescription is shared in a third-party pharmacy.

Figure 14:
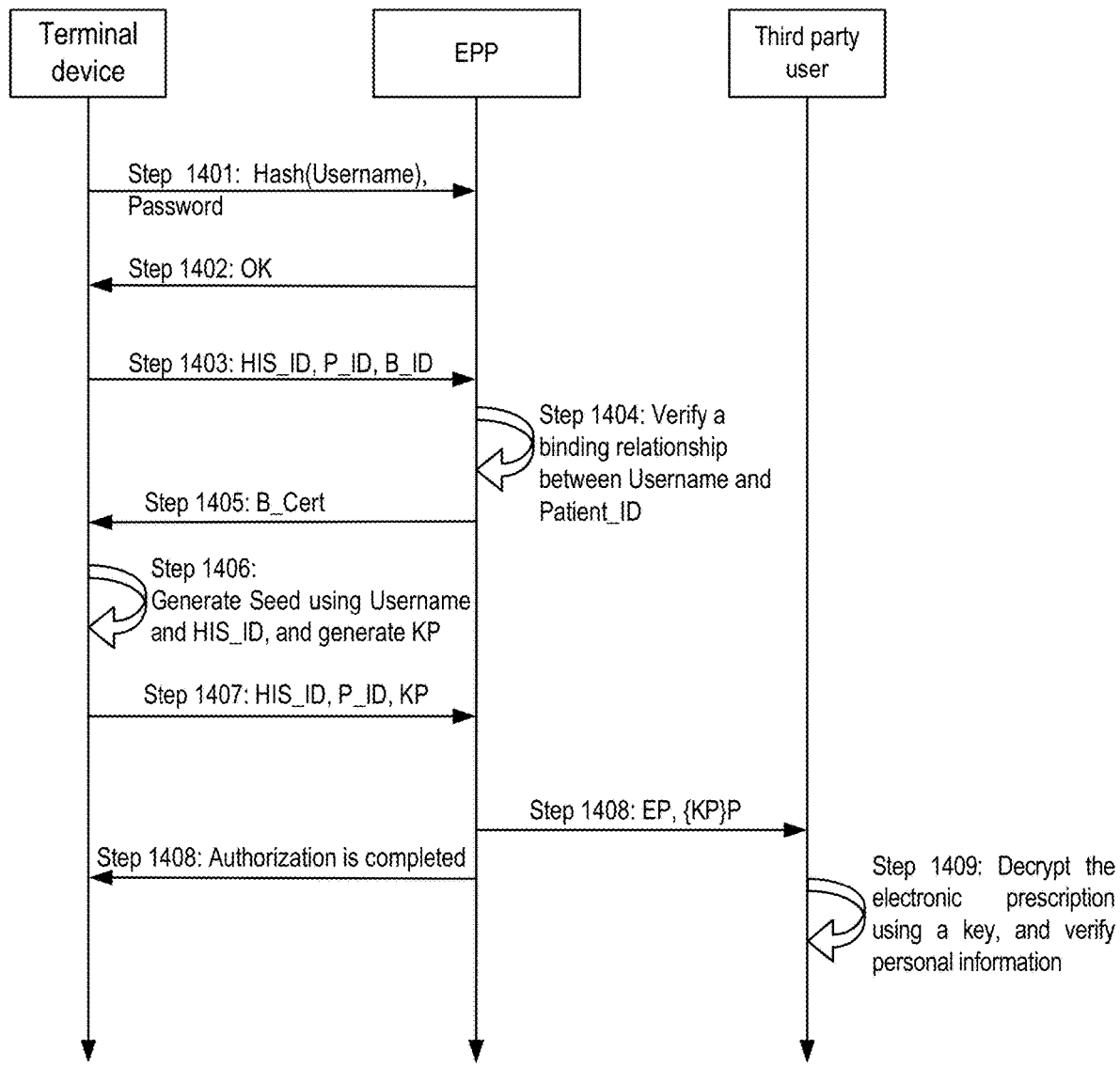
FIG. 14 is an activity diagram of a method for acquiring an electronic file according to some embodiments of the disclosure.

FIG. 14 is an activity diagram of a method for acquiring an electronic file according to some embodiments of the disclosure. In some situations, other participants, for example, pharmacies or other doctors, than patients themselves need to be authorized to view prescriptions. These entities should be trusted third parties that register with an EPP platform and are approved, and should have digital certificates. When a third-party user needs to acquire an electronic prescription of a patient-user, as shown in FIG. 6, the method includes the following steps.

Step 1401: The user logs in to the EPP using a hash value of a mobile phone number and a login password through a terminal device.

Step 1402: The EPP returns confirmation information indicating successful login after performing verification.

Step 1403: The user sends a first request message to the EPP through the terminal device, where the first request message includes a hospital code HIS_ID, a prescription number P_ID, and a third identifier B_ID of the third-party user.

Step 1404: The EPP confirms whether the third-party user has the right to view the prescription and whether a user login name has a binding relationship with a user registration name on an HIS.

Step 1405: The EPP returns a digital certificate B_Cert of the third-party user to the terminal device.

Step 1406: The user generates Seed from login information and a first identifier through the terminal device, and generates a second encryption key KP corresponding to the electronic prescription based on the prescription number, Seed, and HIS_ID.

Step 1407: The terminal device generates a digital envelope using a public key of the third-party user, encrypts the second encryption key KP corresponding to the electronic prescription, and sends the hospital number HIS_ID and the prescription number P_ID together to the EPP.

Step 1408: The EPP searches for the electronic prescription according to information such as the prescription number P_ID, sends the electronic prescription and the second encryption key KP that is used for encrypting the electronic prescription and encrypted using the public key P of the third-party user to the third-party user, and informs the terminal device that the authorization is already completed.

Step 1409: The third-party user decrypts the encrypted second encryption key using a private key of the third-party user, so as to obtain the second encryption key KP, decrypts private information in the electronic prescription using the second encryption key KP, and then verifies the validity of the electronic prescription through the private information.

In this process, a second encryption key is shared with a third-party user through a digital envelope of the third-party user, so as to avoid the flow of reacquiring the second encryption key by the third-party user. Since the EPP does not obtain any personal private information of a patient-user in the whole process and the third-party user obtains private information of only one electronic prescription, other encryption keys of the patient-user cannot be inferred accordingly, and thus more personal privacy of the patient-user cannot be obtained. Those skilled in the art can understand that this embodiment is also applicable to distribution of an electronic prescription to other third parties, for example, doctors or insurance companies.

In the embodiment shown in FIG. 12 to FIG. 14, since personal information of a relevant user in an electronic prescription needs to be released to a third-party when necessary, data such as the personal information needs to be desensitized by means of encryption, and when any electronic prescription is transferred from the HIS to the EPP, personal information should be encrypted using a second encryption key generated by the HIS before being transferred to the EPP platform. Information contained in a desensitized electronic prescription saved by the EPP platform may be represented as follows:

HIS_ID: an identity of the HIS (plaintext)
Patient_ID: a user registration name (which may also be referred to as a patient identity) (plaintext)
Pr_ID: an identity of the electronic prescription (plaintext)
Patient_Info: personal information in the electronic prescription (stored in an encrypted manner)
Prescription_Info: content of the electronic prescription (stored in plaintext)

By means of the aforementioned encrypted storage, it can be ensured that personal information involved in an electronic prescription is saved on the EPP platform in an encrypted manner. Since a second encryption key is saved on the HIS, personal information of the user cannot be acquired if the electronic prescription is stolen from the EPP platform.

Figure 15:
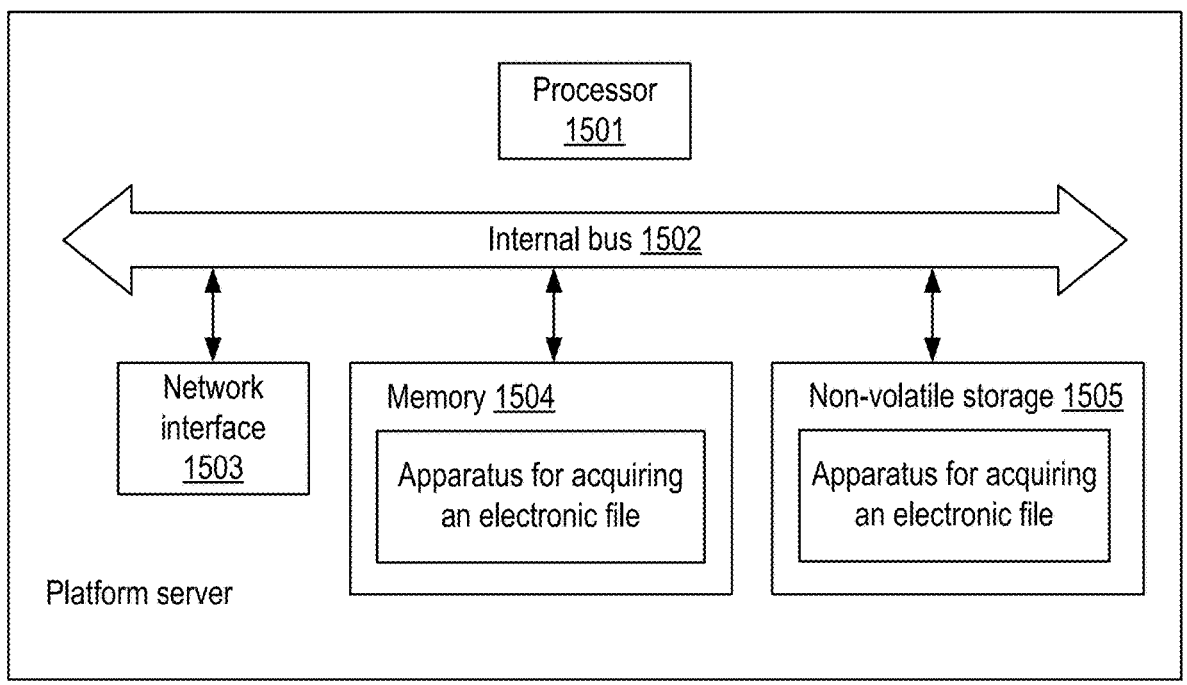
FIG. 15 is a diagram of a terminal device according to some embodiments of the disclosure.

Corresponding to the aforementioned method for acquiring an electronic file shown in FIG. 1 to FIG. 4, the disclosure further provides a diagram of a terminal device according to some embodiments of the disclosure shown in FIG. 15. Referring to FIG. 15, the terminal device includes a processor 1501, an internal bus 1502, a network interface 1503, a memory 1504, and a non-volatile storage 1505 on the hardware level, and certainly may also include hardware required by other services. The processor 1501 reads a corresponding computer program into the memory 1504 from the non-volatile storage 1505 and then runs the computer program, so as to form an apparatus for acquiring an electronic file on the logical level. Certainly, in addition to the software implementation, the present disclosure does not exclude other implementations, for example, using a logical device or a combination of software and hardware. That is to say, execution bodies of the following processing flows are not limited to logical units, and may also be hardware or logical devices.

Figure 16:
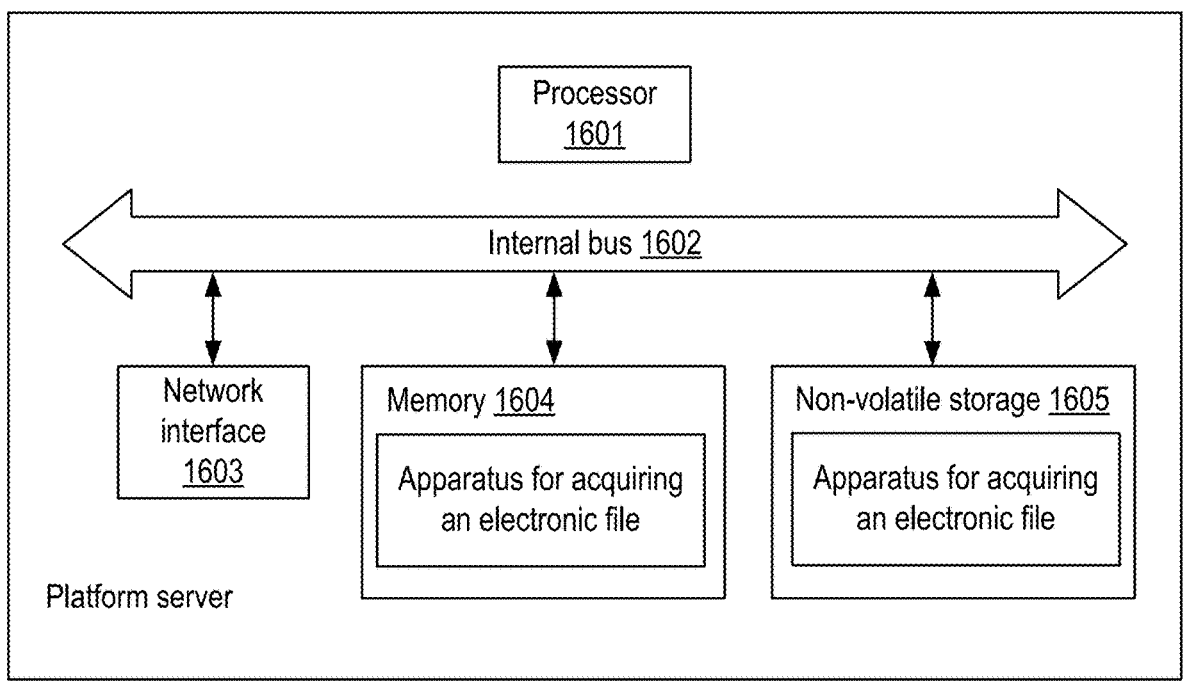
FIG. 16 is a diagram of a platform server according to some embodiments of the disclosure.

Corresponding to the aforementioned method for acquiring an electronic file shown in FIG. 5A to FIG. 8, the present disclosure further provides a diagram of a platform server according some embodiments of the present disclosure shown in FIG. 16. Referring to FIG. 16, the platform server includes a processor 1601, an internal bus 1602, a network interface 1603, a memory 1604, and a non-volatile storage 1605 on the hardware level, and certainly may also include hardware required by other services. The processor 1601 reads a corresponding computer program into the memory 1604 from the non-volatile storage 1605 and then runs the computer program, so as to form an apparatus for acquiring an electronic file on the logical level. Certainly, in addition to the software implementation, the present disclosure does not exclude other implementations, for example, using a logical device or a combination of software and hardware. That is to say, execution bodies of the following processing flows are not limited to logical units, and may also be hardware or logical devices.

Figure 17:
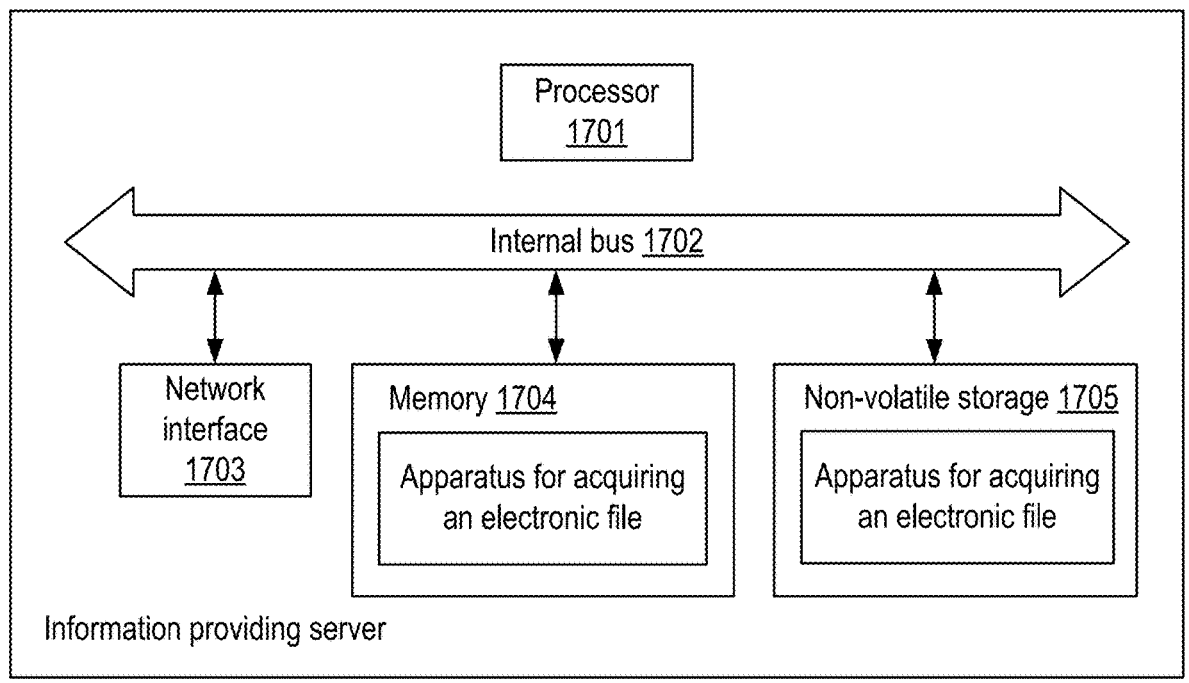
FIG. 17 is a diagram of an information providing server according to some embodiments of the disclosure.

Corresponding to the aforementioned method for acquiring an electronic file shown in FIG. 9 to FIG. 11, the present disclosure further provides a diagram of an information providing server according some embodiments of the disclosure shown in FIG. 17. Referring to FIG. 17, the information providing server includes a processor 1701, an internal bus 1702, a network interface 1703, a memory 1704, and a non-volatile storage 1705 on the hardware level, and certainly may also include hardware required by other services. The processor 1701 reads a corresponding computer program into the memory 1704 from the non-volatile storage 1705 and then runs the computer program, so as to form an apparatus for acquiring an electronic file on the logical level. Certainly, in addition to the software implementation, the present disclosure does not exclude other implementations, for example, using a logical device or a combination of software and hardware. That is to say, execution bodies of the following processing flows are not limited to logical units, and may also be hardware or logical devices.

Figure 18:
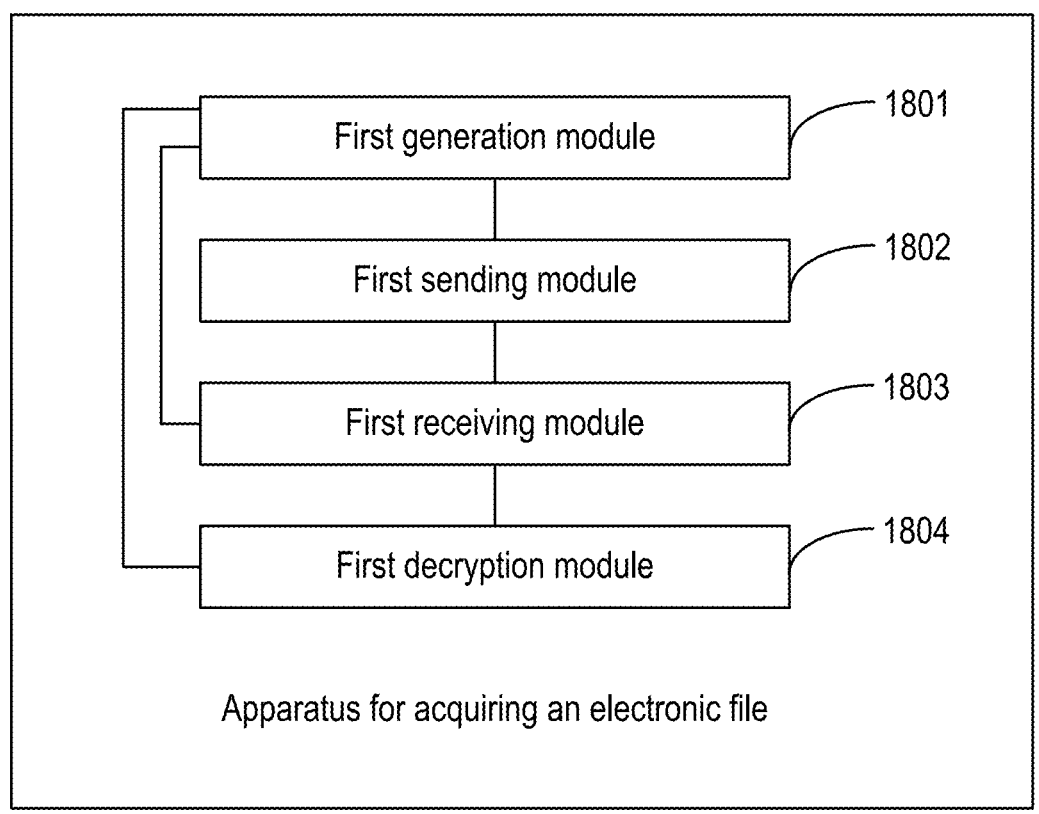
FIG. 18 is a diagram of an apparatus for acquiring an electronic file according to some embodiments of the disclosure.

FIG. 18 is a diagram of an apparatus for acquiring an electronic file according to some embodiments of the disclosure. The apparatus may be executed by a terminal device. In a software implementation, the apparatus for acquiring an electronic file may include: a first generation module 1801, a first sending module 1802, a first receiving module 1803, and a first decryption module 1804, where the first generation module 1801 is configured to generate a first encryption key according to login information of a user of the terminal device at the time of logging in to a platform server and a first identifier corresponding to an information providing server that provides the electronic file, where the information providing server is used for providing the electronic file to the terminal device; the first sending module 1802 is configured to send a first request message for acquiring the electronic file to the platform server, where the first request message includes the first identifier and a second identifier of the electronic file; the first receiving module 1803 is configured to receive the electronic file encrypted using a second encryption key and returned by the platform server according to the login information used by the first generation module 1801 and the first request message sent by the first sending module 1802, where the second encryption key is generated from the first encryption key, the first identifier, and the second identifier; and the first decryption module 1804 is configured to generate a first decryption key according to the first encryption key generated by the first generation module 1801, and decrypt, using the first decryption key, the electronic file encrypted using the second encryption key and received by the first receiving module 1803, so as to obtain the decrypted electronic file.

Figure 19:
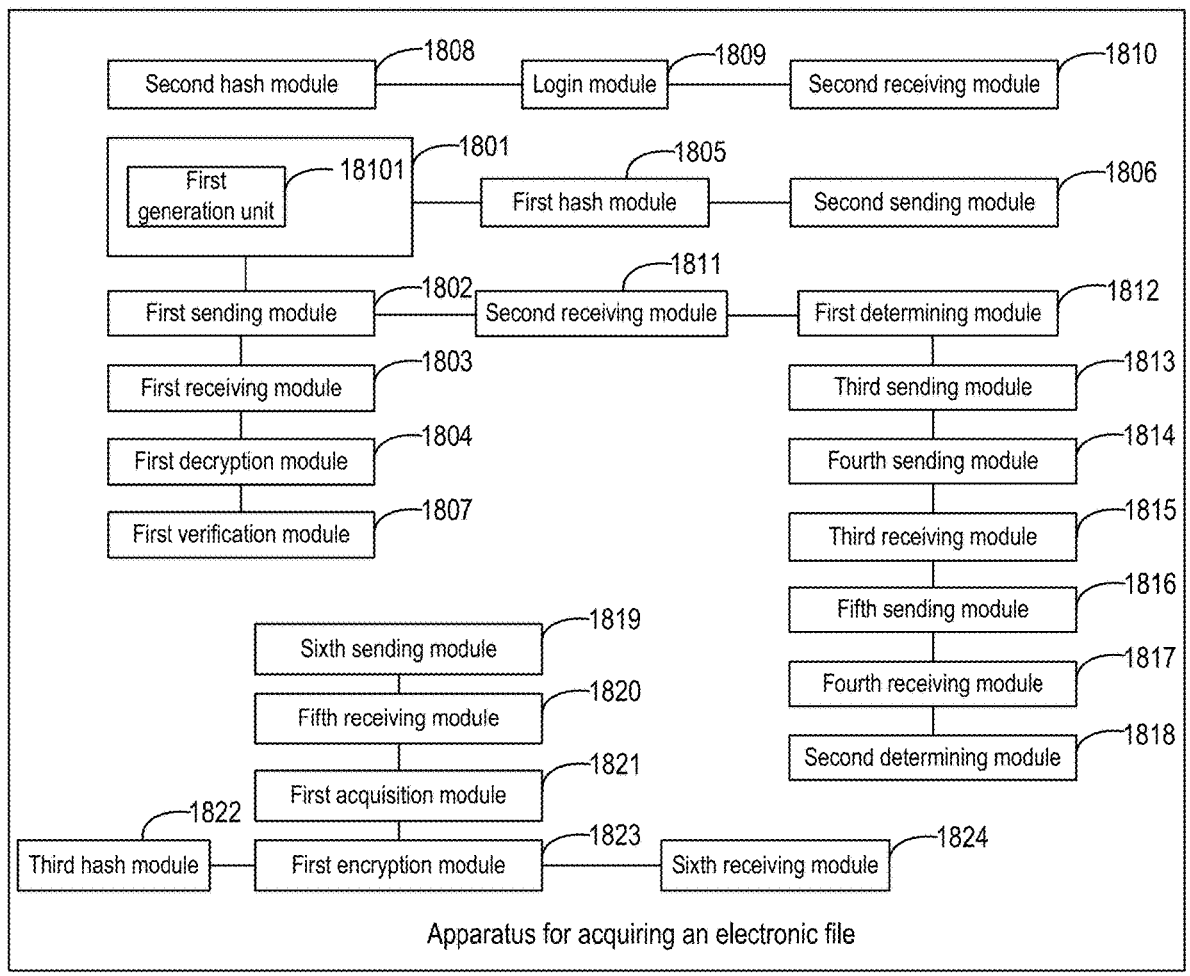
FIG. 19 is a diagram of an apparatus for acquiring an electronic file according to some embodiments of the disclosure.

FIG. 19 is a diagram of an apparatus for acquiring an electronic file according to some embodiments of the disclosure. On the basis of the embodiment shown in FIG. 18, the first generation module 1801 may include: a first generation unit 18101, configured to perform a hash operation on a user login name and a login password that are included in the login information and the first identifier corresponding to the information providing server that provides the electronic file, so as to generate the first encryption key.

In one embodiment, the apparatus may further include: a first hash module 1805, configured to perform a hash operation on the first encryption key generated by the first generation module 1801, the first identifier, and the second identifier to obtain a hash value; and a second sending module 1806, configured to send the hash value obtained by the first hash module 1805 to the platform server, so as to verify the validity of the first request message according to the hash value after the platform server forwards the hash value to the information providing server.

In one embodiment, the apparatus may further include: a first verification module 1807, configured to, after the first decryption module 1804 performs decryption to obtain the decrypted electronic file, perform validity verification on user information in the electronic file.

In one embodiment, the apparatus may further include: a second hash module 1808, configured to perform a hash operation on the login information used by the first generation module 1801, so as to obtain a user login name after the hash operation; a login module 1809, configured to log in to the platform server using the login information after the hash operation of the second hash module 1808; and a second receiving module 1810, configured to receive a first confirmation message returned by the platform server according to the login information of the login module 1809 after the hash operation.

In one embodiment, the apparatus further includes: a second receiving module 1811, configured to, after the first sending module 1802 sends the first request message for acquiring the electronic file to the platform server, receive a second confirmation message returned by the platform server after verifying a binding relationship between the first identifier and a user login name in the login information, where if the second confirmation message indicates that the first identifier has the binding relationship with the user login name, the first receiving module 1803 performs the step of receiving the electronic file encrypted using a second encryption key and returned by the platform server according to the first request message.

In one embodiment, the apparatus may further include: a first determining module 1812, configured to, if the second confirmation message received by the second receiving module 1811 indicates that the first identifier does not have the binding relationship with the user login name, determine a digital envelope corresponding to a digital certificate of the information providing server according to the first identifier; and a third sending module 1813, configured to send the first encryption key and the user login name to the platform server after encrypting them using the digital envelope that is determined by the first determining module 1812.

In one embodiment, the apparatus may further include: a fourth sending module 1814, configured to send user information corresponding to the user login name that is included in the login information to a trusted third-party platform when the platform server returns a third-party authentication notification to the terminal device according to the first encryption key and the user login name that are encrypted and sent by the third sending module 1813; a third receiving module 1815, configured to receive a digital signature from the trusted third-party platform after the trusted third-party platform verifies the user information that is sent by the fourth sending module 1814, where the digital signature is obtained by the trusted third-party platform signing a timestamp and a hash value of the user information using a private key of the trusted third-party platform; and a fifth sending module 1816, configured to send to the platform server an authentication result of the digital signature of the trusted third-party platform that is received by the third receiving module 1815.

In one embodiment, the apparatus may further include: a fourth receiving module 1817, configured to, after the platform server verifies the validity of the authentication result that is sent by the fifth sending module 1816, receive a hash value of the user information and the first encryption key and a notification message indicating that the first identifier is successfully bound to the user login name that are returned by the platform server according to the authentication result; and a second determining module 1818, configured to determine the authenticity of the hash value of the user information and the first encryption key according to the user information sent by the fourth sending module 1817 and the first encryption key generated by the first generation module 1801, so as to confirm that the first identifier is successfully bound to the user login name included in the login information.

In one embodiment, the apparatus may further include: a sixth sending module 1819, configured to send a second request message for acquiring an electronic file to the platform server, where the second request message includes the first identifier, the second identifier, and a third identifier of a third-party user; a fifth receiving module 1820, configured to, after the platform server confirms that the third identifier sent by the sixth sending module 1819 has the right to view the electronic file and that the first identifier has a binding relationship with the user login name included in the login information, receive a digital certificate of the third-party user that is returned by the platform server; a first acquisition module 1821, configured to acquire a public key of the third-party user from the digital certificate that is received by the fifth receiving module 1820; a third hash module 1822, configured to generate the second encryption key through a hash operation according to the first encryption key generated by the first generation module 1801, the first identifier, and the second identifier; and a first encryption module 1823, configured to encrypt, using the public key of the third-party user that is acquired by the first acquisition module 1821, the second encryption key generated by the third hash module 1822, and send the first identifier, the second identifier, and the encrypted second encryption key to the platform server.

In one embodiment, the apparatus may further include: a sixth receiving module 1824, configured to, after the platform server finds the electronic file according to the second identifier, receive a notification message confirming that third-party authorization is completed that is returned by the platform server.

Figure 20:
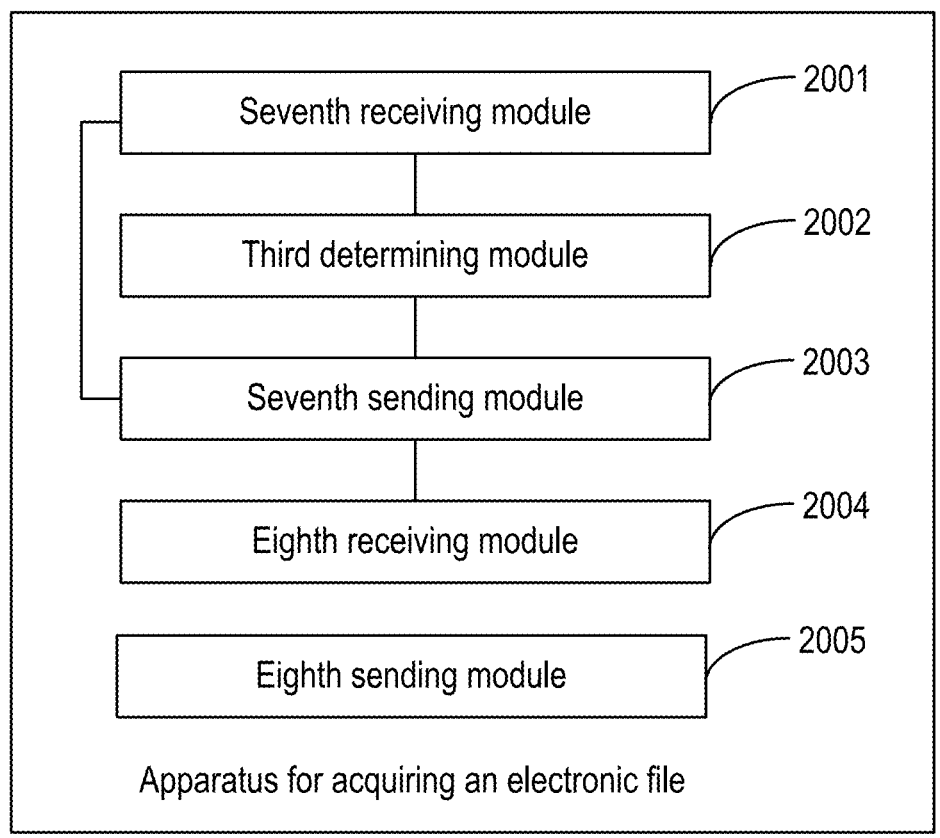
FIG. 20 is a diagram of an apparatus for acquiring an electronic file according to some embodiments of the disclosure.

FIG. 20 is a diagram of an apparatus for acquiring an electronic file according to some embodiments of the disclosure. The apparatus may be executed by a platform server. In a software implementation, the apparatus for acquiring an electronic file may include: a seventh receiving module 2001, a third determining module 2002, a seventh sending module 2003, an eighth receiving module 2004, and an eighth sending module 2005, where the seventh receiving module 2001 is configured to receive a first request message from a terminal device for acquiring an electronic file, where the first request message includes a first identifier corresponding to an information providing server that provides the electronic file and a second identifier corresponding to the electronic file; the third determining module 2002 is configured to determine a user registration name of a user of the terminal device on the information providing server through login information of the user on the platform server and the first identifier that is carried in the first request message received by the seventh receiving module 2001; the seventh sending module 2003 is configured to send the first identifier and the second identifier that are carried in the first request message received by the seventh receiving module 2001 and the user registration name that is determined by the third determining module 2002 to the information providing server after digitally signing them; the eighth receiving module 2004 is configured to receive the electronic file encrypted by the information providing server using a second encryption key, where the second encryption key is generated from a first encryption key and the first identifier that is carried in the first request message received by the seventh receiving module 2001, and the first encryption key is generated according to the login information of the user of the terminal device logging in to the platform server and the first identifier; and the eighth sending module 2005 is configured to send the electronic file encrypted using the second encryption key and received by the eighth receiving module 2004 to the terminal device.

Figure 21:
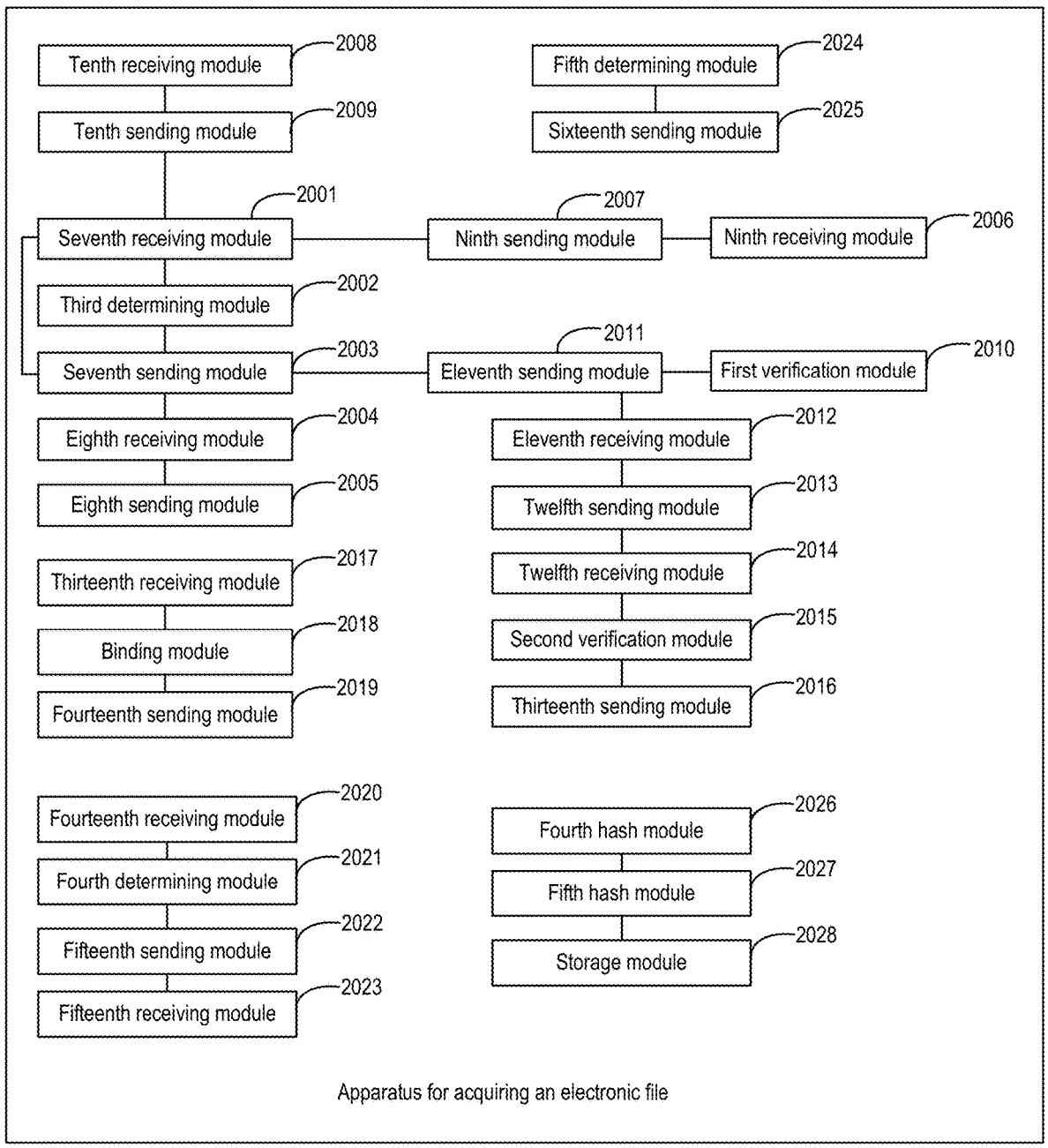
FIG. 21 is a diagram of an apparatus for acquiring an electronic file according to some embodiments of the disclosure.

FIG. 21 is a diagram of an apparatus for acquiring an electronic file according to some embodiments of the disclosure. On the basis of the embodiment shown in FIG. 20, the apparatus may further include: a ninth receiving module 2006, configured to receive a hash value from the terminal device, where the hash value is obtained by performing a hash operation on the first encryption key, the first identifier, and the second identifier corresponding to the electronic file; and a ninth sending module 2007, configured to send the hash value received by the ninth receiving module 2006 to the information providing server after signing the hash value, so that the information providing server verifies, according to the hash value, the validity of the first request message received by the seventh receiving module 2001.

In one embodiment, the apparatus may further include: a tenth receiving module 2008, configured to receive login information subjected to a hash operation from the terminal device; and a tenth sending module 2009, configured to send a first confirmation message to the terminal device after performing validity verification on the login information received by the tenth receiving module 2008.

In one embodiment, the apparatus may further include: a first verification module 2010, configured to verify a binding relationship between the first identifier and a user login name that is included in the login information according to the first request message before the seventh sending module 2003 sends the first encryption key, the first identifier, and the second identifier to the information providing server after digitally signing them; and an eleventh sending module 2011, configured to return a second confirmation message to the terminal device, where if the second confirmation message indicates that the first identifier has the binding relationship with the user login name, the seventh sending module 2003 performs the step of sending the first encryption key, the first identifier, and the second identifier to the information providing server after digitally signing them.

In one embodiment, the apparatus may further include: an eleventh receiving module 2012, configured to, if the second confirmation message sent by the eleventh sending module 2011 indicates that the first identifier does not have the binding relationship with the user login name, receive a digital envelope from the terminal device, where the digital envelope contains the first encryption key and a card identifier corresponding to the user login name on the information providing server, and the digital envelope is generated by the terminal device according to a digital certificate of the information providing server; a twelfth sending module 2013, configured to return a third-party authentication notification to the terminal device after verifying the digital envelope received by the eleventh receiving module 2012; and a twelfth receiving module 2014, configured to receive a digital signature obtained by the terminal device on the trusted third-party platform according to the third-party authentication notification that is returned by the twelfth sending module 2013 to the terminal device, where the digital signature of the trusted third-party platform is obtained by the trusted third-party platform signing a timestamp and a hash value of the user information using a private key of the trusted third-party platform.

In one embodiment, the apparatus may further include: a second verification module 2015, configured to perform validity verification on the digital signature of the trusted third-party platform that is received by the twelfth receiving module 2014; and a thirteenth sending module 2016, configured to, after the verification performed by the second verification module 2015 on the digital signature of the trusted third-party platform is passed, send the first encryption key and the card identifier that are encrypted using the digital envelope to the information providing server.

In one embodiment, the apparatus may further include: a thirteenth receiving module 2017, configured to receive the user registration name of the user login name registered with the information providing server, a hash value of the first encryption key, and the first identifier that are returned by the information providing server; a binding module 2018, configured to establish a binding relationship between the user registration name received by the thirteenth receiving module 2017 and the user login name; and a fourteenth sending module 2019, configured to send to the terminal device a hash value of the user login name and the first encryption key, the first identifier, and a confirmation message indicating successful binding of the binding relationship by the binding module 2018, where the terminal device is used for verifying the authenticity of the hash value according to the first encryption key and the user login name.

In one embodiment, the apparatus may further include: a fourteenth receiving module 2020, configured to receive a second request message from the terminal device for acquiring an electronic file, where the second request message includes the first identifier, the second identifier, and a third identifier of a third-party user; a fourth determining module 2021, configured to confirm whether the third identifier received by the fourteenth receiving module 2020 has the right to view the electronic file and whether the first identifier has a binding relationship with the user login name; a fifteenth sending module 2022, configured to return a digital certificate of the third-party user to the terminal device after the fourth determining module 2021 confirms that the third identifier has the right to view the electronic file and that the first identifier has the binding relationship with the user login name; and a fifteenth receiving module 2023, configured to receive the first identifier, the user login name, and the encrypted second encryption key from the terminal device, where the second encryption key is generated through a hash operation according to the first encryption key, the first identifier, and the user login name and encrypted using a public key in the digital certificate of the third-party user that is received by the fifteenth sending module 2022.

In one embodiment, the apparatus may further include: a fifth determining module 2024, configured to determine the electronic file according to the second identifier; and a sixteenth sending module 2025, configured to send the electronic file determined by the fifth determining module 2024 and the second encryption key encrypted using the public key of the third-party user to the third-party user, where a terminal of the third-party user decrypts, according to a private key of the third-party user, the second encryption key encrypted using the public key of the third-party user, so as to obtain the second encryption key, and decrypts private information in the electronic file according to the second encryption key.

In one embodiment, the apparatus may further include: a fourth hash module 2026, configured to perform a first hash operation on the user login name in the login information that is received by the tenth receiving module 2008, so as to obtain login information after the first hash operation; a fifth hash module 2027, configured to perform a second hash operation using a fixed key on the login information after the first hash operation performed by the fourth hash module 2026; and a storage module 2028, configured to store the login information subjected to the second hash operation performed by the fifth hash module 2027.

Figure 22:
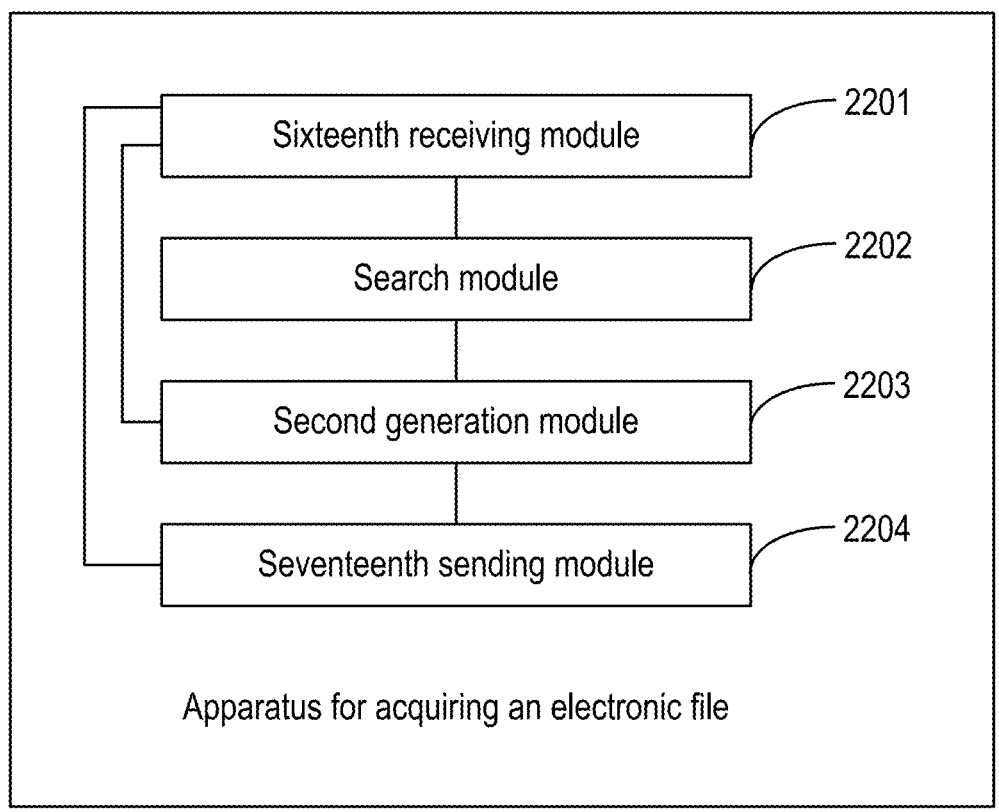
FIG. 22 is a diagram of an apparatus for acquiring an electronic file according to some embodiments of the disclosure.

FIG. 22 is a diagram of an apparatus for acquiring an electronic file according to some embodiments of the disclosure. The apparatus may be executed by an information providing server. In a software implementation, the apparatus for acquiring an electronic file may include: a sixteenth receiving module 2201, a search module 2202, a second generation module 2203, and a seventeenth sending module 2204, where the sixteenth receiving module 2201 is configured to receive a third request message from a platform server for acquiring an electronic file, where the third request message includes a first identifier corresponding to the information providing server and a second identifier of the electronic file; the search module 2202 is configured to search for the electronic file according to the second identifier received by the sixteenth receiving module 2201; the second generation module 2203 is configured to generate a second encryption key for encrypting the electronic file according to the first identifier and the second identifier that are received by the sixteenth receiving module 2201 and a first encryption key, where the first encryption key is generated from login information of the terminal device on the platform server and the first identifier; and the seventeenth sending module 2204 is configured to send the first identifier and the second identifier that are carried in the third request message received by the sixteenth receiving module 2201 and the electronic file that is encrypted using the second encryption key generated by the second generation module 2203 to the platform server.

Figure 23:
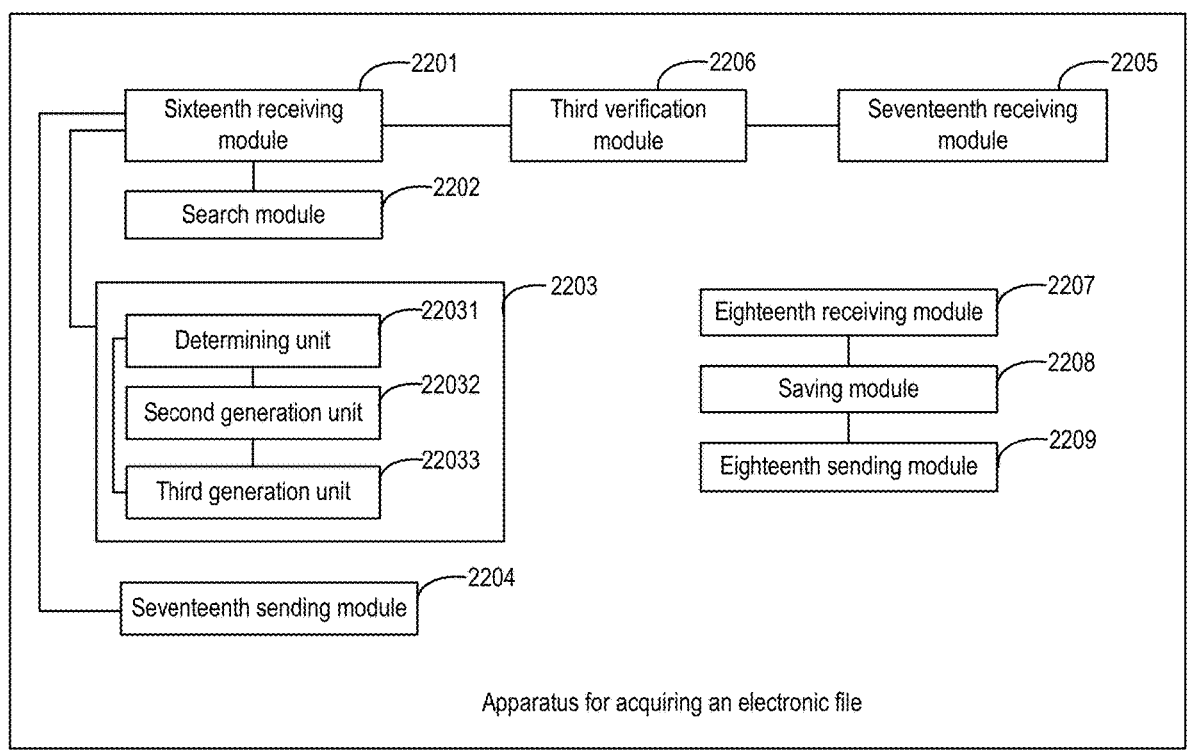
FIG. 23 is a diagram of an apparatus for acquiring an electronic file according to some embodiments of the disclosure.

FIG. 23 is a diagram of an apparatus for acquiring an electronic file according to some embodiments of the disclosure. On the basis of the embodiment shown in FIG. 22, the apparatus may further include: a seventeenth receiving module 2205, configured to receive a hash value from the terminal device that is forwarded by the platform server, where the hash value is obtained by performing a hash operation on the first encryption key, the first identifier, and the second identifier corresponding to the electronic file; and a third verification module 2206, configured to perform validity verification, through the hash value received by the seventeenth receiving module 2205, on the third request message received by the sixteenth receiving module 2201.

In one embodiment, the second generation module 2203 may include: a determining unit 22031, configured to determine whether a user of the terminal device stores multiple electronic files on the information providing server; a second generation unit 22032, configured to, if the determining unit 22031 determines that one electronic file is stored on the information providing server, generate the second encryption key corresponding to the electronic file according to the first encryption key, the first identifier, and the second identifier; and a third generation unit 22033, configured to, if the determining unit 22031 determines that two or more electronic files are stored on the information providing server, sequentially generate second encryption keys respectively corresponding to the two or more electronic files according to the first encryption key, the first identifier, the second identifier, and second decryption keys corresponding to adjacent electronic files.

In one embodiment, the apparatus may further include: an eighteenth receiving module 2207, configured to, after the platform server performs validity verification on a digital signature of a trusted third-party platform, receive a user login name encrypted by the platform server using a digital envelope, where the digital envelope is generated by the terminal device from a card identifier of the user on the information providing server using a digital certificate corresponding to the information providing server; a saving module 2208, configured to, after verifying the validity of user information of the terminal device and the validity of association with the card identifier, save the first encryption key and extract a user registration name of the user login name registered with the information providing server; and an eighteenth sending module 2209, configured to send the user registration name saved by the saving module 2208, a hash value of the first encryption key, and the second identifier to the platform server.

As can be seen from the aforementioned embodiments, in the embodiments of the disclosure, a terminal device generates a first encryption key based on information known to a user such as a first identifier, a user login name, and a login password, shares the first encryption key as a seed key (Seed) with an information providing server, and the terminal device does not need to save the first encryption key, thereby improving encryption security and user experience. For private information in an electronic file to be protected, the information providing server may generate a second encryption key based on the first encryption key, and data to be encrypted in the electronic file is encrypted on the information providing server side and transferred to a platform server, so the user does not need to acquire the second encryption key and can infer the second encryption key from the first encryption key, and therefore the complexity of interaction between devices is reduced, and the platform server cannot obtain the encrypted data in the electronic file in the whole process of acquiring the electronic file.

Those skilled in the art can easily derive other implementation solutions of the present disclosure after considering the specification and practicing the embodiments disclosed herein. The present disclosure is intended to cover any variations, uses, or adaptive changes of the present disclosure. These variations, uses, or adaptive changes follow general principles of the present disclosure and include common knowledge or conventional technical means in the art that is not disclosed in the present disclosure. The specification and embodiments are considered exemplary only, and the true scope and spirit of the present disclosure will be reflected by the following claims.

It should be noted that the term "include", "comprise", or any other variation thereof is intended to encompass a non-exclusive inclusion so that a process, method, commodity, or device that includes a series of elements includes not only those elements but also other elements not explicitly listed, or elements that are inherent to such a process, method, commodity, or device. The element defined by the statement "including one . . . ", without further limitation, does not preclude the presence of additional identical elements in the process, method, commodity, or device that includes the element.

The above descriptions are merely preferred embodiments of the present disclosure, and are not intended to limit the present disclosure. Any alterations, equivalent substitutions, improvements and the like made within the spirit and principle of the present disclosure shall fall within the protection scope of the present disclosure.

What is claimed is:

1. A method comprising:
   generating, at a terminal device, a first encryption key based on login information of a user and a first identifier corresponding to an information providing server that provides an electronic file;
   sending, by the terminal device, a first request message to a platform server, wherein the first request message includes the first identifier, a second identifier of the electronic file, and a third identifier of a third-party user;
   receiving, by the terminal device, a digital certificate of the third-party user that is returned by the platform server after the platform server confirms that the third identifier has the right to view the electronic file;
   receiving, by the terminal device, the electronic file encrypted using a second encryption key, wherein the second encryption key is generated from the first encryption key, the first identifier, and the second identifier;
   generating, by the terminal device, a first decryption key according to the first encryption key;
   decrypting, by terminal device using the first decryption key, the electronic file encrypted using the second encryption key, and
   receiving, by the terminal device, a notification message from the platform server confirming that third-party authorization is completed after the platform server finds the electronic file according to the second identifier.

2. The method of claim 1, wherein the login information of a user comprises the username and password of the user associated with the information providing server.

3. The method of claim 2, wherein generating a first encryption key based on login information of a user and a first identifier corresponding to an information providing server that provides an electronic file comprises:
   performing, by the terminal device, a hash operation on the username and password of the user to obtain hashed login information;
   sending, by the terminal device, the hashed login information to the platform server;
   receiving, at the terminal device, a first confirmation message returned by the platform server according to the hashed login information; and
   generating, at the terminal device, the first encryption key by performing a second hash operation on a user login name and a login password included in the login information and the identifier.

4. The method of claim 3, wherein sending the first request message to a platform server comprises generating, by the terminal device, a hash value by performing a third hash operation on the first encryption key, the first identifier, and the second identifier and wherein the first request message further includes the hash value.

5. The method of claim 1, further comprising performing, by the terminal device, validity verification on user information included in the electronic file after obtaining the decrypted electronic file.

6. The method of claim 1, further comprising:
   determining, by the terminal device, a digital envelope corresponding to a digital certificate of the information providing server according to the first identifier;
   sending, by the terminal device, the first encryption key and a card identifier corresponding to the user information to the platform server after encrypting them using the digital envelope;
   sending, by the terminal device, the user information to a trusted third-party platform when the platform server returns a third-party authentication notification to the terminal device;
   receiving, by the terminal device, a digital signature from the trusted third-p arty platform after the trusted third-party platform verifies the user information, wherein the digital signature is obtained by the trusted third-party platform signing a timestamp and a hash value of the user information using a private key of the trusted third-party platform;
   sending, by the terminal device, an authentication result of the digital signature to the platform server;

receiving, by the terminal device, a hash value of the user information and the first encryption key and a notification message indicating that the first identifier is successfully bound to the user login name returned by the platform server according to the authentication result after the platform server verifies the validity of the authentication result; and determining, by the terminal device, the authenticity of the hash value to confirm that the first identifier is successfully bound to a user login name included in the login information.

7. The method of claim 1, further comprising:
acquiring, by the terminal device, a public key of the third-party user from the digital certificate;
generating, by the terminal device, the second encryption key through a hash operation according to the first encryption key, the first identifier, and the second identifier; and
encrypting, by the terminal device, the second encryption key using the public key of the third-party user, and sending the first identifier, the second identifier, and the encrypted second encryption key to the platform server.

8. The method of claim 1, wherein the electronic file comprises an electronic prescription, wherein the platform server comprises an electronic prescription platform, and wherein the information providing server comprises a hospital information system.

9. A method comprising:
generating, at a terminal device, a first encryption key based on login information of a user and a first identifier corresponding to an information providing server that provides an electronic file;
sending, at the terminal device, a first request message to a platform server, wherein the first request message includes the first identifier, a second identifier of the electronic file, and a third identifier of a third-party user;
receiving, at the terminal device, a digital certificate of the third-party user that is returned by the platform server after the platform server confirms that the third identifier has the right to view the electronic file;
receiving, at the terminal device, the electronic file encrypted using a second encryption key, wherein the second encryption key is generated from the first encryption key, the first identifier, and the second identifier;
generating, at the terminal device, a first decryption key according to the first encryption key; and
decrypting, at the terminal device, using the first decryption key, the electronic file encrypted using the second encryption key.

10. The method of claim 9, wherein the login information of a user comprises the username and password of the user associated with the information providing server.

11. The method of claim 10, wherein the generating a first encryption key based on login information of a user and a first identifier corresponding to an information providing server that provides an electronic file further comprises:
performing, at the terminal device, a hash operation on the username and password of the user to obtain hashed login information;
sending, at the terminal device, the hashed login information to the platform server;
receiving a first confirmation message returned by the platform server according to the hashed login information; and generating, at the terminal device, the first encryption key by performing a second hash operation on a user login name and a login password included in the login information and the identifier.

12. The method of claim 11, wherein sending a first request message to the platform server comprises generating, at the terminal device, a hash value by performing a third hash operation on the first encryption key, the first identifier, and the second identifier and wherein the first request message further includes the hash value.

13. The method of claim 9, further comprising, performing, at the terminal device, validity verification on user information included in the electronic file after obtaining the decrypted electronic file.

14. The method of claim 9, further comprising:
determining, at the terminal device, a digital envelope corresponding to a digital certificate of the information providing server according to the first identifier;
sending, at the terminal device, the first encryption key and a card identifier corresponding to the user information to the platform server after encrypting them using the digital envelope;
sending, at the terminal device, the user information to a trusted third-party platform when the platform server returns a third-party authentication notification to the terminal device;
receiving, at the terminal device, a digital signature from the trusted third-party platform after the trusted third-party platform verifies the user information, wherein the digital signature is obtained by the trusted third-party platform signing a timestamp and a hash value of the user information using a private key of the trusted third-party platform;
sending, at the terminal device, an authentication result of the digital signature to the platform server;
receiving, at the terminal device, a hash value of the user information and the first encryption key and a notification message indicating that the first identifier is successfully bound to the user login name returned by the platform server according to the authentication result after the platform server verifies the validity of the authentication result; and
determining, at the terminal device, the authenticity of the hash value to confirm that the first identifier is successfully bound to a user login name included in the login information.

15. The method of claim 9, further comprising:
acquiring, at the terminal device, a public key of the third-party user from the digital certificate;
generating, at the terminal device, the second encryption key through a hash operation according to the first encryption key, the first identifier, and the second identifier;
encrypting, at the terminal device, the second encryption key using the public key of the third-party user, and sending the first identifier, the second identifier, and the encrypted second encryption key to the platform server; and
receiving, at the terminal device, a notification message from the platform server confirming that third-party authorization is completed after the platform server finds the electronic file according to the second identifier.

16. A method comprising:
receiving, at a platform server, a first request message from a terminal device for acquiring an electronic file, wherein the first request message includes a first identifier corresponding to an information providing server that provides the electronic file, a second identifier corresponding to the electronic file and a third identifier of a third-party user;

determining, by the platform server, a user registration name of a user of the terminal device on the information providing server through login information of the user on the platform server and the first identifier;

sending, by the platform server, the first identifier, the second identifier, and the user registration name to the information providing server after digitally signing them;

receiving, at the platform server, the electronic file encrypted by the information providing server using a second encryption key, wherein the second encryption key is generated from a first encryption key and the first identifier, the first encryption key generated according to the login information of the user of the terminal device logging in to the platform server and the first identifier;

sending the electronic file encrypted using the second encryption key to the terminal device;

confirming, at the platform server, that the third-party user has the right to view the electronic file and that the first identifier has a binding relationship with a user login name; and sending, by the platform server, the electronic file and the second encryption key that is encrypted using the public key of the third-party user to the third-party user.

17. The method of claim 16, further comprising:
returning, at the platform server, a digital certificate of the third-party user to the terminal device;

receiving, at the platform server, the first identifier, the user login name, and an encrypted second encryption key from the terminal device, wherein the second encryption key is generated through a hash operation according to the first encryption key, the first identifier, and the user login name and encrypted using a public key in the digital certificate of the third-party user; and identifying, at the platform server, the electronic file according to the second identifier.

18. The method of claim 16, further comprising:
receiving, at the platform server, a hash value from the terminal device, the hash value generated by performing a hash operation on the first encryption key, the first identifier, and the second identifier corresponding to the electronic file;

performing, at the platform server, validity verification on a third request message using the hash value;

determining, at the platform server, whether a user of the terminal device stores multiple electronic files on an information providing server after the validity verification on the third request message is passed;

generating, at the platform server, the second encryption key corresponding to the electronic file according to the first encryption key, the first identifier, and the second identifier if one electronic file is stored; and sequentially generate, at the platform server, second encryption keys respectively corresponding to the electronic files according to the first encryption key, the first identifier, the second identifier, and second decryption keys corresponding to adjacent electronic files if two or more electronic files are stored.

19. The method of claim 16, further comprising:
receiving, at the platform server, the user registration name of the user login name registered with the information providing server, a hash value of the first encryption key, and the first identifier that are returned by the information providing server;

establishing, by the platform server, a binding relationship between the user registration name and the user login name; and sending, by the platform server, a hash value of the user login name and the first encryption key, the first identifier, and a confirmation message indicating successful binding to the terminal device, wherein the terminal device is used for verifying the authenticity of the hash value according to the first encryption key and the user login name.

* * * * *